(12) United States Patent
Aghassian

(10) Patent No.: US 9,044,617 B2
(45) Date of Patent: *Jun. 2, 2015

(54) EXTERNAL CHARGER FOR A MEDICAL IMPLANTABLE DEVICE USING FIELD INDUCING COILS TO IMPROVE COUPLING

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/024,266

(22) Filed: Sep. 11, 2013

(65) Prior Publication Data

US 2014/0012352 A1 Jan. 9, 2014

Related U.S. Application Data

(63) Continuation of application No. 13/653,185, filed on Oct. 16, 2012, now Pat. No. 8,548,590, which is a continuation of application No. 12/579,740, filed on Oct. 15, 2009, now Pat. No. 8,311,638.

(51) Int. Cl.
*A61N 1/00* (2006.01)
*A61N 1/378* (2006.01)
*A61N 1/36* (2006.01)

(52) U.S. Cl.
CPC ........... *A61N 1/3787* (2013.01); *A61N 1/36071* (2013.01)

(58) Field of Classification Search
CPC .................. A61N 1/3787; A61N 1/36071
USPC ................................... 607/29–33, 61
See application file for complete search history.

(56) References Cited

U.S. PATENT DOCUMENTS

| | | | |
|---|---|---|---|
| 5,314,453 | A | 5/1994 | Jeutter |
| 5,749,909 | A | 5/1998 | Schroeppel et al. |
| 6,553,263 | B1 | 4/2003 | Meadows et al. |
| 7,774,069 | B2 | 8/2010 | Olson et al. |
| 8,010,205 | B2 | 8/2011 | Rahman et al. |
| 8,244,367 | B2 | 8/2012 | Wahlstrand et al. |
| 2005/0165461 | A1 | 7/2005 | Takeda et al. |
| 2007/0060980 | A1 | 3/2007 | Strother et al. |
| 2008/0027293 | A1 | 1/2008 | Vodermayer et al. |
| 2009/0069869 | A1 | 3/2009 | Stouffer et al. |

(Continued)

FOREIGN PATENT DOCUMENTS

| | | |
|---|---|---|
| JP | H10-122806 | 5/1998 |
| WO | 2003034095 A1 | 4/2003 |

*Primary Examiner* — Scott Getzow
(74) *Attorney, Agent, or Firm* — Lewis & Reese, PLLC

(57) ABSTRACT

By incorporating magnetic field-inducing position determination coils (PDCs) in an external charger, it is possible to determine the position of an implantable device by actively inducing magnetic fields using the PDCs and sensing the reflected magnetic field from the implant. In one embodiment, the PDCs are driven by an AC power source with a frequency equal to the charging coil. In another embodiment, the PDCs are driven by an AC power source at a frequency different from that of the charging coil. By comparing the relative reflected magnetic field strengths at each of the PDCs, the position of the implant relative to the external charger can be determined. Audio and/or visual feedback can then be communicated to the patient to allow the patient to improve the alignment of the charger.

32 Claims, 17 Drawing Sheets

(56) References Cited

U.S. PATENT DOCUMENTS

| | | | |
|---|---|---|---|
| 2009/0112291 A1* | 4/2009 | Wahlstrand et al. | 607/61 |
| 2009/0118796 A1 | 5/2009 | Chen et al. | |
| 2010/0201315 A1 | 8/2010 | Oshimi et al. | |
| 2010/0204756 A1 | 8/2010 | Aghassian | |
| 2011/0004278 A1 | 1/2011 | Aghassian et al. | |
| 2011/0093048 A1 | 4/2011 | Aghassian | |

* cited by examiner

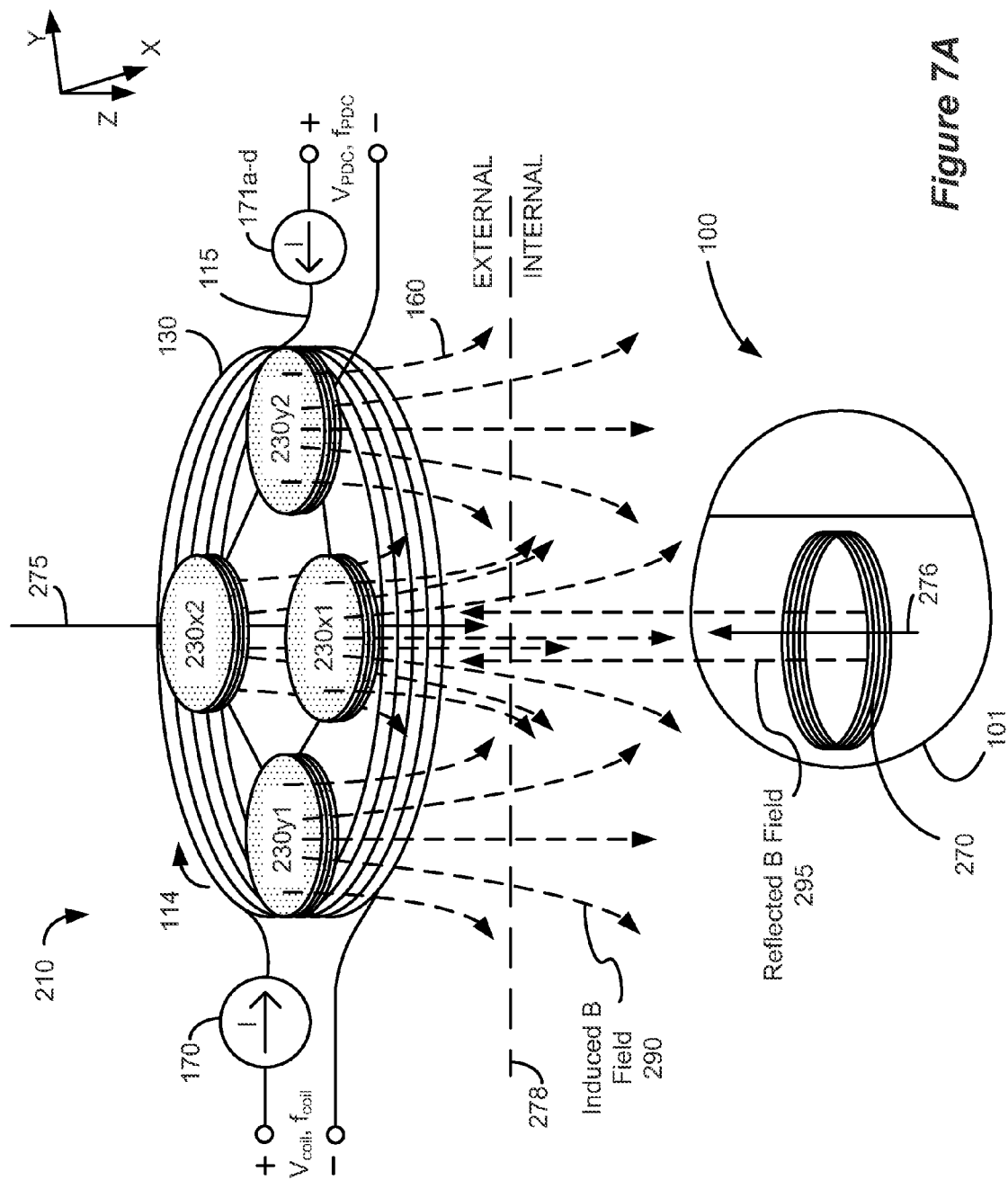

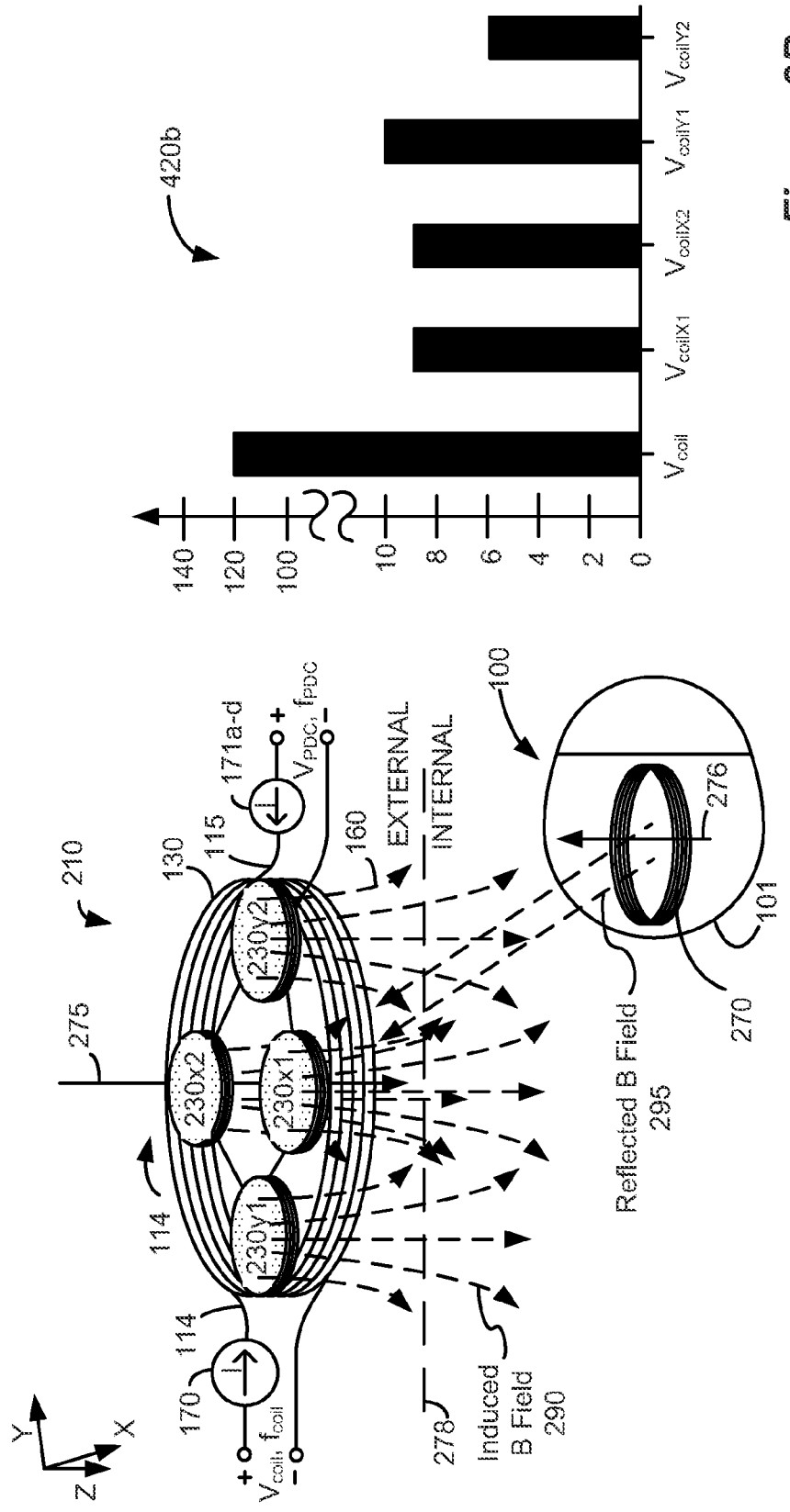

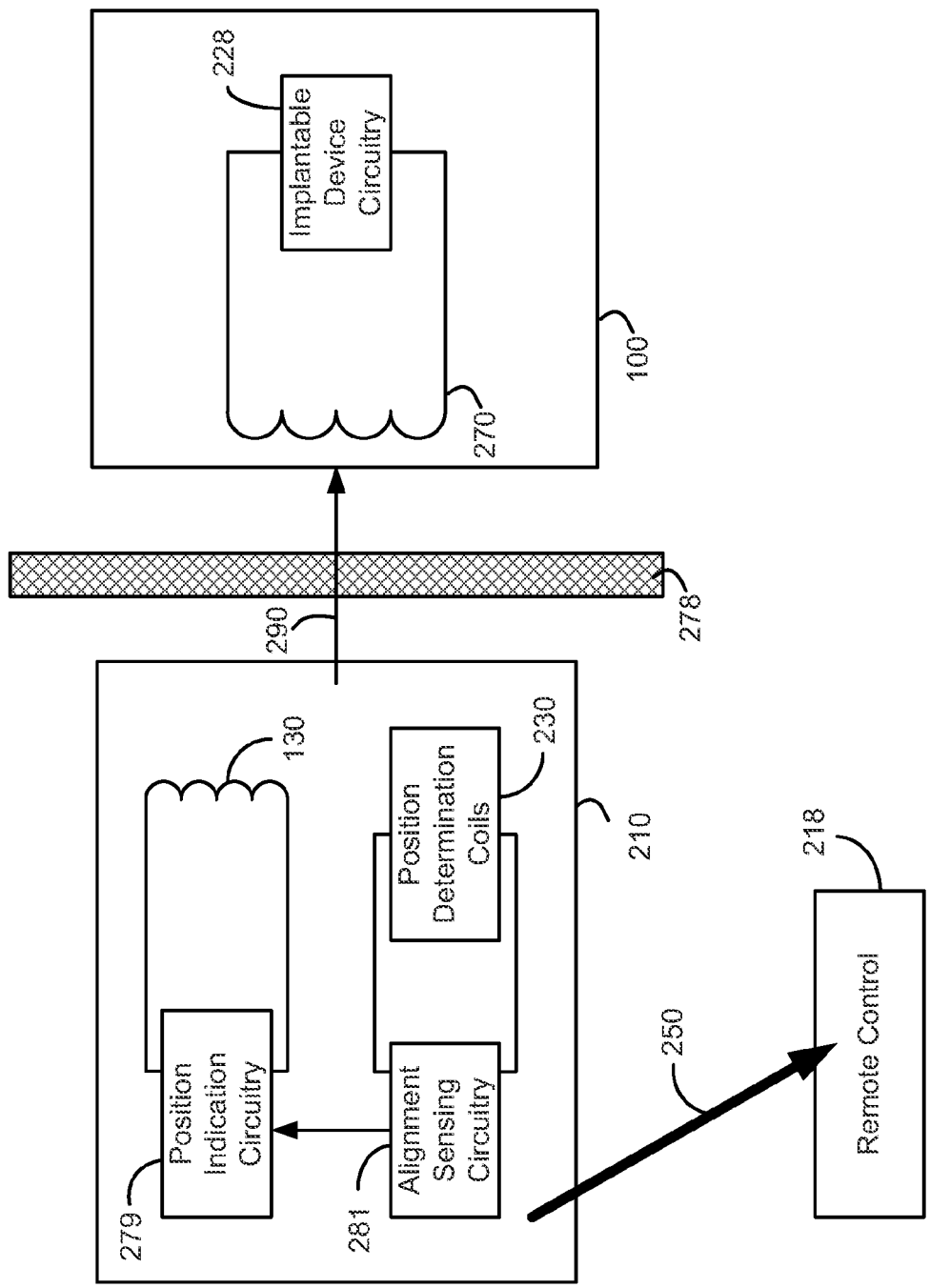

EXTERNAL CHARGER FOR A MEDICAL IMPLANTABLE DEVICE USING FIELD INDUCING COILS TO IMPROVE COUPLING

CROSS-REFERENCE TO RELATED APPLICATION

This is a continuation of U.S. patent application Ser. No. 13/653,185, filed Oct. 16, 2012, which was a continuation of U.S. patent application Ser. No. 12/579,740, filed Oct. 15, 2009 (now U.S. Pat. No. 8,311,638), which are incorporated herein by reference in its entirety and to which priority are claimed. This application is also related to commonly-assigned U.S. Pat. No. 8,473,066, which is hereby incorporated by reference in its entirety.

FIELD OF THE INVENTION

The present invention relates to techniques for providing improved alignment between an external charger and an implantable device.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. patent application Ser. No. 11/177,503, filed Jul. 8, 2005.

Spinal cord stimulation is a well-accepted clinical method for reducing pain in certain populations of patients. An SCS system typically includes an Implantable Pulse Generator (IPG), electrodes, at least one electrode lead, and, optionally, at least one electrode lead extension. As shown in FIG. 1, the electrodes 106, which reside on a distal end of the electrode lead 102, are typically implanted along the dura 70 of the spinal cord 19, and the IPG 100 generates electrical pulses that are delivered through the electrodes 106 to the nerve fibers within the spinal column 19. Electrodes 106 are arranged in a desired pattern and spacing to create an electrode array 110. Individual wires 112 within one or more electrode leads 102 connect with each electrode 106 in the array 110. The electrode lead(s) 102 exit the spinal column 19 and may attach to one or more electrode lead extensions 120. The electrode lead extensions 120, in turn, are typically tunneled around the torso of the patient to a subcutaneous pocket where the IPG 100 is implanted. Alternatively, the electrode lead 102 may directly connect with the IPG 100.

As should be obvious, an IPG needs electrical power to function. Such power can be provided in several different ways, such as through the use of a rechargeable or non-rechargeable battery or through electromagnetic (EM) induction provided from an external charger, or from combinations of these and other approaches, which are discussed in further detail in U.S. Pat. No. 6,553,263 ("the '263 patent"). Perhaps the favorite of these approaches is to use a rechargeable battery in the IPG, such as a lithium-ion battery or a lithium-ion polymer battery. Such a rechargeable battery can generally supply sufficient power to run an IPG for a sufficient period (e.g., a day or more) between recharging. Recharging can occur through the use of EM induction, in which EM fields are sent by an external charger to the IPG. Thus, when the battery needs recharging, the patient in which the IPG is implanted can activate the external charger to transcutaneously (i.e., through the patient's flesh) charge the battery (e.g., at night when the patient is sleeping or during other convenient periods).

The basics of such a system are shown in FIG. 2. As shown, the system comprises, in relevant part, the external charger 208 and IPG 100. A primary coil 130 in the charger 208 produces an EM field 290 capable of transcutaneous transmission through a patient's flesh 278. The external charger 208 may be powered by any known means, such as via a battery or by plugging into a wall outlet, for example. The EM field 290 is met at the IPG 100 by another coil 270, and accordingly, an AC voltage is induced in that coil 270. This AC voltage in turn is rectified to a DC voltage at a rectifier 682, which may comprise a standard bridge circuit. (There may additionally be data telemetry associated with the EM field 290, but this detail is ignored as impertinent to the present disclosure). The rectified DC voltage is, in turn, sent to a charge controller and protection circuit 684, which operates generally to regulate the DC voltage and to produce either a constant voltage or constant current output as necessary for recharging the battery 180.

FIG. 3 shows further details of external charger 208 with the top portion of the housing removed. Further details concerning external chargers can be found in U.S. patent application Ser. No. 11/460,955, filed Jul. 28, 2006. As shown in FIG. 3, electrical current 114 flowing in a counterclockwise direction through the primary coil 130 induces a magnetic field 290 having a prominent portion in a direction perpendicular to the plane in which the primary coil 130 lies. Primary coil 130 is typically formed of many turns of copper Litz wire, but the individual turns are not shown in FIG. 3 for clarity. Thus, when a face of the case of the external charger 208 is oriented in close proximity to an implanted device, such that the primary coil 130 is parallel to a corresponding coil within the IPG 100, the magnetic field generated by the primary coil 130 induces an electrical current within a corresponding coil to charge a battery within, or otherwise provide power, to the IPG 100.

This system is akin to a transformer where the primary coil is in the external charger 208 and secondary coil in the IPG 100. The efficiency of this coupling is largely dependent upon the alignment between the two coils, which efficiency can be expressed as a coupling factor, k. Achieving a good coupling factor is essential for optimizing efficiency of the inductive link. Not only does good coupling increase the power transferred to the implant, it minimizes heating in the implant, and also reduces the power requirements of the external charger, which reduces heating of the charger and allows a smaller form factor. Proper coupling is also essential if there is to be any data telemetry between the external charger 208 and the implant.

Operation of the external charger 208 in the prior art typically involves the use of audio feedback to the user. Thus, when charging begins, the external charger 208 produces induced field 290 and begins searching for the IPG 100, as will be explained in more detail herein. An audio transducer in the external charger 208 would provide an intermittent audible sound (e.g., beeping) when coupling was poor between the charger 208 and the IPG 100, which beeping would alert the user to move the external charger relative to the IPG. Once the positioning and coupling were improved, the charger 208 would stop beeping, and the location of the charger 208 would be held in place over the IPG 100 by using double-side adhesive pads or a belt. If the charger 208 again became poorly positioned relative to the IPG 100, the audio transducer would again start beeping, so that the position of the charger 208 relative to the IPG 100 could again be readjusted. A back-telemetry link from the IPG 100 would communicate to the charger 208 when the IPG battery was fully charged, which condition can again be audibly signaled to the patient.

As noted earlier, proper alignment between an external charger and an implant is essential for proper system function, energy transfer, and safety to the patient. However, this has heretofore been difficult to achieve. In particular, it has been noticed by the inventors that it is difficult for prior art external chargers to differentiate between a deeply-implanted device that is well aligned with respect to the charger, and a shallowly-implanted device that is poorly aligned with respect to the charger. Either scenario appears the same to the external charger 208. As a result, the patient will only know that the coupling is poor, but will not know how to remedy this situation apart from trial-and-error re-positioning of the charger.

Given these shortcomings, the art of implantable devices would benefit from techniques for achieving improved coupling between an external charger and an implantable device that provide: the ability to accurately indicate the relative position of the charger to the implant; increased charging efficiency; faster charging rates; increased patient safety and comfort; lower power requirements; and a smaller form factor. This disclosure presents a solution to this problem involving the use of position determination coils that actively induce their own magnetic fields.

BRIEF DESCRIPTION OF THE DRAWINGS

FIG. 7A shows a typical configuration, wherein the primary coil of an improved external charging device is located at or near the outer surface of the patient's skin and the secondary coil of an implantable medical device is located near the inner surface of the patient's skin.

FIGS. 9A-9B illustrate typical configurations, wherein the primary coil of an improved external charging device is located at or near the outer surface of the patient's skin and the secondary coil of an implantable medical device is located near to or far from the inner surface of the patient's skin.

FIG. 10 shows a system comprising an improved external charger for charging an implantable pulse generator, including the alignment sensing and position indication circuitry of the external charger.

DETAILED DESCRIPTION

The description that follows relates to use of the invention within a spinal cord stimulation (SCS) system. However, it is to be understood that the invention is not so limited. Rather, the invention may be used with any type of implantable medical device that could benefit from improved alignment between an external charger and the implantable device. For example, the present invention may be used as part of a system employing an external charger configured to charge a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder subluxation, etc. Moreover, the technique can be used in non-medical and/or non-implantable devices or systems as well, i.e., in any device or system in which proper coupling between a primary and second device is necessary or desirable.

As noted earlier, achieving proper coupling between an external charger and an implant can be difficult, as it is hard for the external charger to differentiate between a deep implant that is well aligned to the external charger and a shallow implant that is misaligned with the external charger. Both scenarios appear the same to the external charger. The present invention provides an improved external charger having improved means for determining the position of the implanted device relative to the charger by actively inducing one or more magnetic fields and measuring the reflected magnetic field from the implanted device.

In one embodiment, the external charger 208 contains position determination coils (PDCs) to help discriminate between deep implants and misaligned implants. Through use of these magnetic field-inducing PDCs, it is possible to determine the position of an implantable device by measuring the amount of reflected magnetic field coming from the implant at each PDC. In one embodiment, a plurality of PDCs are arranged within the charge coil in a plane or planes parallel to the charge coil. By comparing the relative reflected magnetic field strengths at each of the PDCs, the position of the implant can be determined. Audio and/or visual feedback can then be communicated to the patient to allow the patient to improve the alignment of the charger.

Figure 4A:
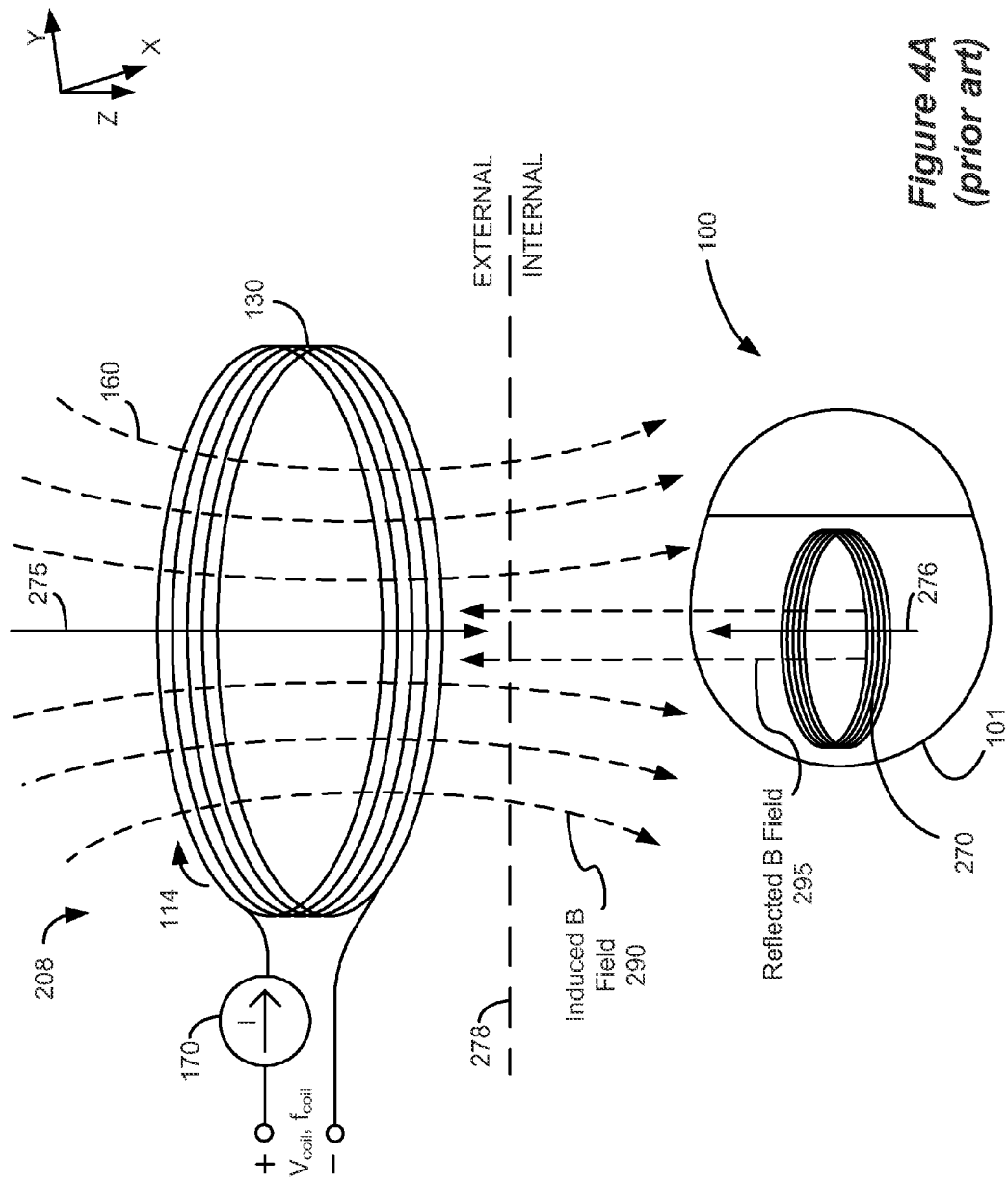
FIGS. 4A-4C illustrate typical configurations, wherein the primary coil of a prior art external charging device is located at or near the outer surface of the patient's skin and the secondary coil of an implantable medical device is located near to or far from the inner surface of the patient's skin.

FIG. 4A shows a primary coil 130 configured for transcutaneously charging the IPG 100 via inductive coupling in accordance with the prior art. As mentioned earlier, the charger 208 comprises a primary coil 130, through which an AC current 114 is passed via an AC current source 170. This current 114 produces induced magnetic field 290, which is illustrated as a plurality of flux lines 160. Flux lines 160 are essentially perpendicular to the surface of the skin 278 where they pass through its surface. In addition, the magnetic flux lines 160 near the center of the primary coil 130 are substantially parallel to the central axis 275 of the coil. A corresponding coil 270 within the IPG 100 transforms this magnetic energy into an electrical current, which is rectified and used by circuitry within the IPG 100 to, e.g., charge a battery 180. The distance between the charger 208 and the IPG 100 is typically on the order of about 1-5 centimeters.

The primary and secondary coils 130 and 270 are substantially in the shape of a circular loop, and are typically formed of several turns of wire, as one skilled in the art will appreciate. However, it will be recognized that the substantially circular shape of the coils 130 and 270 are merely illustrative. The turns of the primary coil 130 define a center opening or aperture having a central axis 275. It will be recognized that the surface of the skin 278 is not always flat. Hence, the central axis 275 of the primary coil 130 is sometimes only approximately or substantially perpendicular to the surface of the skin 278.

The induced magnetic field 290 produces eddy currents in the IPG's typically metallic case 101 or in other conductive structures within the IPG 100. Such eddy currents operate to produce a reflected magnetic field 295, which operates to change the mutual inductance of the primary coil 130, effectively "detuning" the coil. Such detuning changes Vcoil, the voltage used to produce the current in the primary coil 130. Accordingly, from monitoring Vcoil, the relative coupling between the external charger 208 and the IPG 100 can be inferred. Vcoil decreases as the coupling increases, which generally occurs when the external charger 208 and the IPG 100 are closer to one another.

Figure 4C:
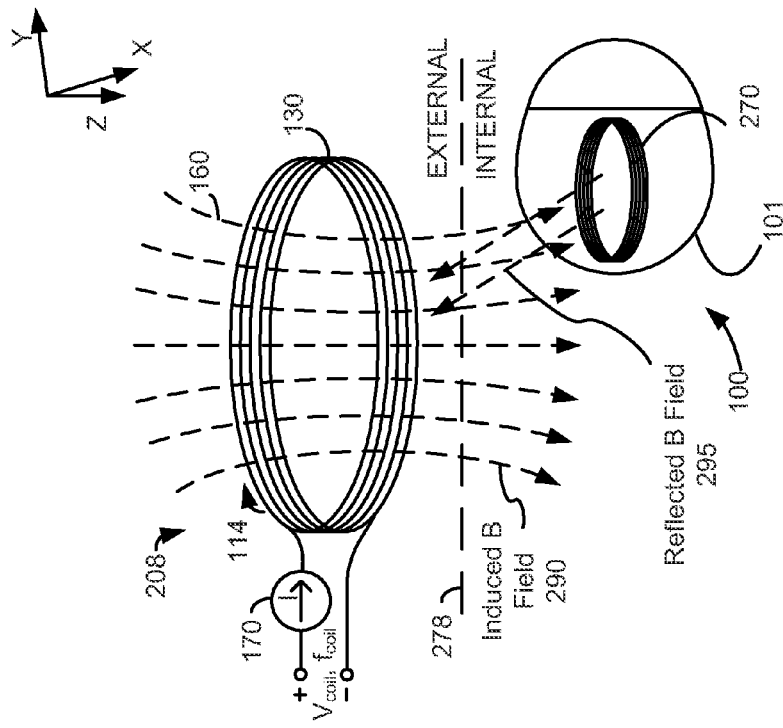
Figure 4B:
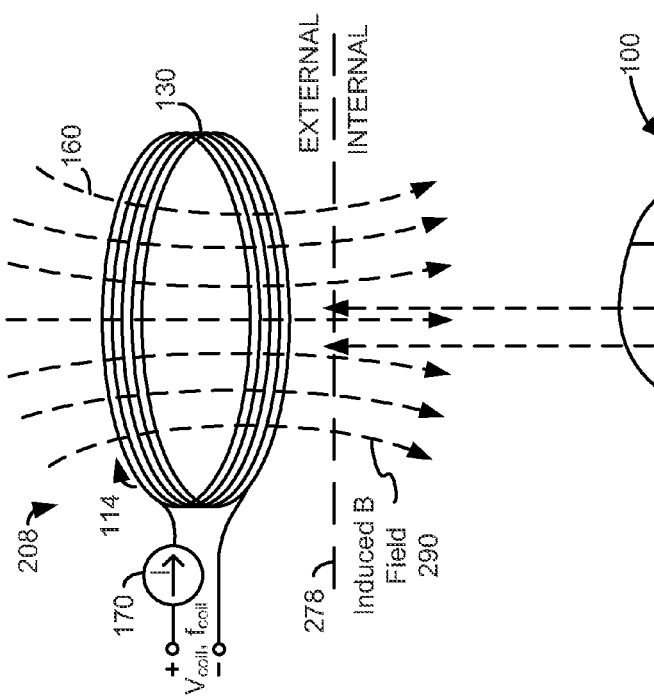

However, this means of monitoring coupling between the external charger 208 and the IPG 100 cannot discern between distance and misalignment, which conditions are illustrated in FIGS. 4B and 4C. FIG. 4B shows an IPG 100 implanted relatively deeply within a patient, but otherwise well aligned from an axial perspective, i.e., coil axes 275 and 276 (see FIG. 4A) are not offset from each other. FIG. 4C, by contrast, shows an IPG 100 implanted relatively shallowly with a patient, but with poor alignment, i.e., coil axes 275 and 276 (see FIG. 4A) are offset to a large degree. In either of these cases, the coupling between the external charger and the IPG 100 will be relatively poor, with the result that Vcoil will not be greatly affected by the IPG 100. However, because Vcoil might be the same in magnitude for both conditions, Vcoil cannot be used to discern between depth (FIG. 4B) and misalignment (FIG. 4C). As a result, Vcoil cannot be used by the external charger 208—and ultimately the patient—to qualify the reason for poor coupling, or how to fix the poor coupling by appropriate repositioning of the external charger 208.

Figure 5A:
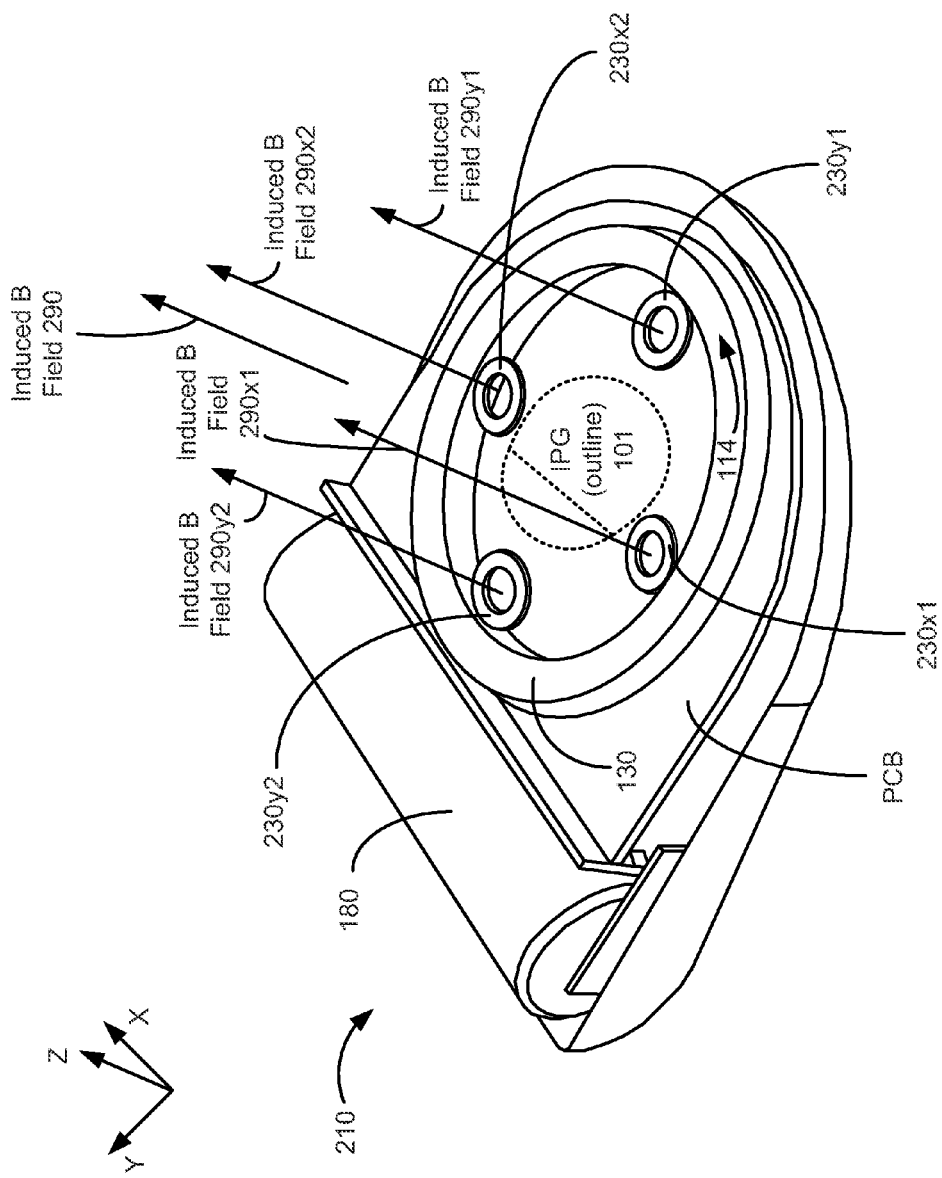
FIG. 5A shows a perspective view of one possible embodiment of an improved external charger for an implantable medical device wherein the position determination coils don't overlap with the outline of the implanted medical device.

FIG. 5A shows one embodiment of an improved external charger 210 with the ability to determine the relative position of an implanted device, and thus maximize coupling by indicating to the user how to improve charger/device alignment. In this embodiment, the four PDCs 230 are arranged into two pairs, 230x1/230x2 and 230y1/230y2, of two active magnetic field inducing coils each. Each PDC is configured to induce its own magnetic field, labeled as: 290x1, 290x2, 290y1, and 290y2. The induced magnetic field of the large charging coil 130 is labeled as 290. Each of the pairs of PDCs 230x and 230y are positioned within primary coil 130 and such that the plurality of PDCs are wound around axes that are parallel to the central axis 275 (FIG. 7A).

The PDCs 230 are designed to induce magnetic fields that are substantially co-axial with their central axes when placed near the surface of the skin 278. By detecting the amount of "detuning," i.e., the decrease in voltage, across each of the PDCs due to the reflected magnetic field 295 caused by the presence of an IPG 100 under the skin's surface, the position of the IPG 100 can be inferred. Each pair of PDCs 230x and 230y may straddle the central axis 275 (FIG. 7A) of the primary coil 130, such that the coils in each pair are equidistant from the central axis 275 and opposite each other. As shown, the pairs 230x and 230y are positioned orthogonally with respect to each other.

Element 101 represents the outline of an IPG that would be implanted within the patient's body. In FIG. 5A, the PDCs 230 are of a small enough size that, when an IPG 100 is perfectly centered within them, the PDCs 230 would only be minimally detuned by the presence of the IPG 100. For example, when the charging coil 130 itself was "detuned" by the presence of the IPG 100, it would be able to indicate to the external charger 210's position indication circuitry 279 (FIG. 7B) that there was an implant somewhere under the surface of the skin in the vicinity of the external charger 210. At that point, the external charger 210 could activate the PDCs 230 to "fine tune" the alignment of the external charger 210 with the IPG 100. If the voltage of each of the PDCs 230 is 10V, for example, the external charger 210 would indicate that it was properly aligned with the IPG 100 when each of the PDCs 230 were simultaneously minimally "detuned" by substantially the same amount, e.g., 2V. If the external charger 210 were misaligned from IPG 100 in any direction, the PDCs 230 that were disproportionately closer to the IPG 100 would, due to the "detuning" effect, register lower voltages than the PDCs 230 that were further away from the IPG 100. By comparing the voltages across each of the PDCs 230, position indication circuitry 279 (FIG. 7B) can indicate to the user the direction that the external charger 210 should be moved in to improve alignment.

Figure 5B:
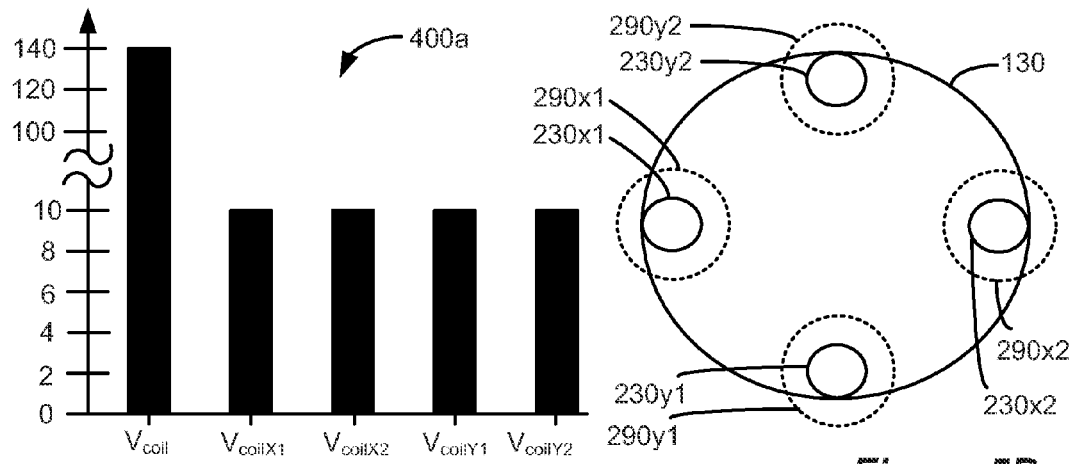
FIGS. 5B-5D show the effects on charging coil voltage and position determination coil voltage due to various charger/implant alignment scenarios.
Figure 5C:
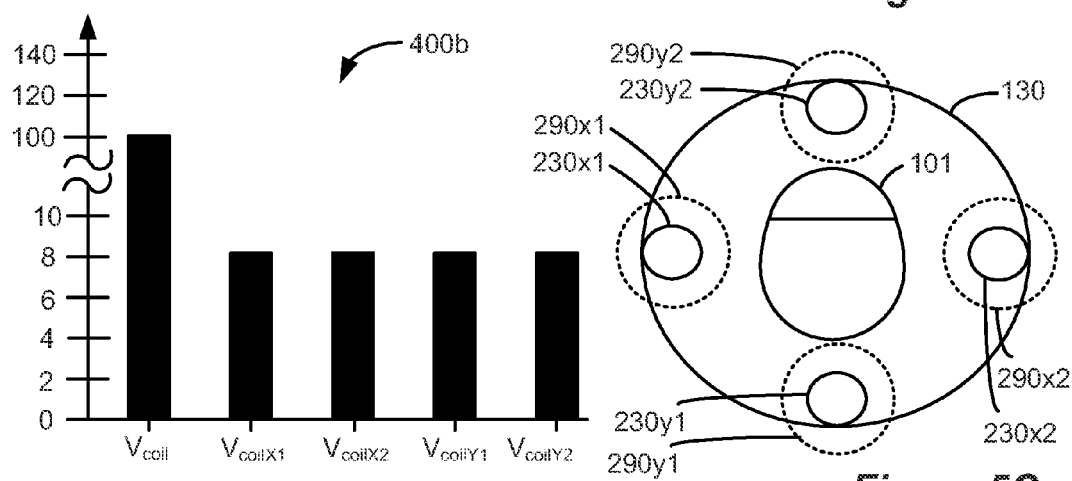
Figure 5D:
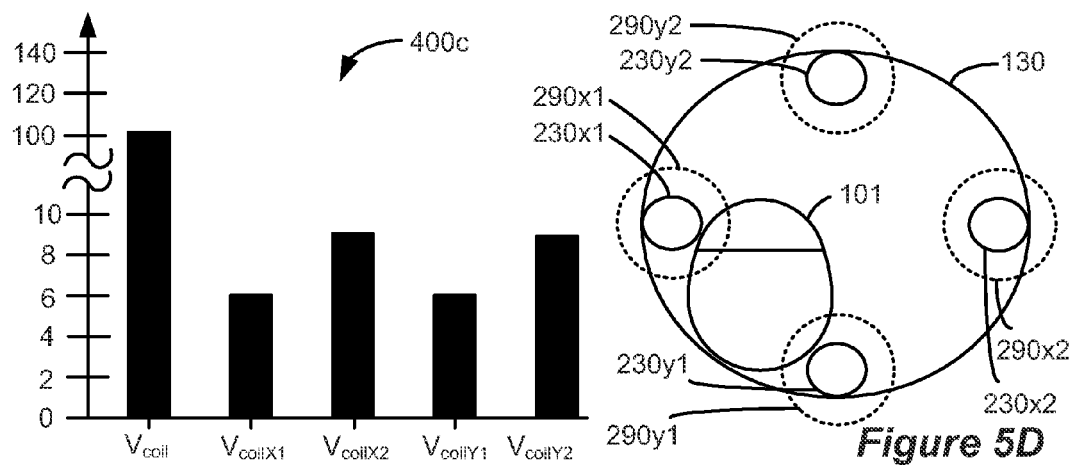

FIGS. 5B-5D show in graphical form the "detuning" effects on the various coils of external charger 210 when an IPG 100 is placed in front of the external charger 210 of FIG. 5A. In FIG. 5B, there is no IPG 100 in the vicinity of the external charger 210's primary coil 130. Thus, there is no detuning of the primary coil 130 and only minimal detuning of the PDCs 230. As such, Vcoil will register as whatever voltage the primary, i.e., charging, coil 130 is being driven at. In graph 400a, this is shown to be 140 volts. Likewise, the PDCs—VcoilX1, VcoilX2, VcoilY1, and VcoilY2—will register at nearly the voltage they are being driven at. In graph 400a, this is shown to be 10 volts. These conditions would be interpreted by position indication circuitry 279 (FIG. 7B) to mean that there was no IPG 100 present.

The dashed lines 290 around each PDC 230 represent roughly the reach of the induced magnetic field of the respective PDC 230. For a PDC 230 with a radius of r, within 2r distance from the PDC 230's center, the PDC magnetic field 290 is especially strong, i.e., it can easily be detected by measurement circuitry or affected by the presence of other magnetic fields. Therefore, if an IPG 100 is present anywhere within 2r distance from the center of the PDC 230, the PDC 230's induced magnetic field may be appreciably detuned, indicating the presence of an implanted device to position indication circuitry 279. Similarly, if two PDCs 230 are closer than 2r distance to each other, each one's induced magnetic field may be affected by the other's, i.e., there may be "cross talk" between the PDCs 230.

In FIG. 5C, the IPG 100 is perfectly aligned within external charger 210's primary coil 130, shown by IPG outline 101. As such, Vcoil will register as being lower than the voltage that the primary, i.e., charging, coil 130 is being driven at due to the detuning effect of the IPG 100. In graph 400b, the charging coil is shown to be detuned from a value of 140 volts to a value of 100 volts, indicating the presence of an implanted IPG 100 in the vicinity of external charge 210. However, the PDCs—VcoilX1, VcoilX2, VcoilY1, and VcoilY2—would register a slightly lower voltage than they were in FIG. 5B. In graph 400b, this is shown to be 8 volts. This occurs because the IPG 100 lies completely within the PDCs 230, and thus the magnetic fields induced by the PDCs 230 are reflected back by the IPG 100, but not as significantly as they would be if there were a greater overlap between the PDCs 230 and the IPG 100. These conditions would be interpreted by position indication circuitry 279 (FIG. 7B) to mean that an IPG 100 was both present and well-aligned with respect to the primary coil 130. In FIG. 5C, there would be almost no "cross talk" from one PDC 230 to another due to the PDC's relatively small radii, as is seen by the lack of overlapping of the dashed magnetic field lines 290.

In FIG. 5D, the IPG 100 is in the vicinity of external charger 210's primary coil 130, but is misaligned, as is shown by IPG outline 101. As such, Vcoil will register as being lower than the voltage that the primary, i.e., charging, coil 130 is being driven at due to the detuning effect of the IPG 100. In graph 400c, the charging coil is shown to be detuned from a value of 140 volts to a value of 100 volts, indicating the presence of an implanted IPG 100 in the vicinity of external charge 210. Two of the PDCs—VcoilX2 and VcoilY2—may register at slightly less than 10V. In graph 400c, this is shown to be 9 volts. However, two of the PDCs—VcoilX1 and VcoilY1—have been detuned to a value of 6 volts. This occurs because the IPG 100 is closer to PDCs 230x1 and 230y1 than it is to the other PDCs. Thus, the magnetic fields induced by PDCs 230x1 and 230y1 are reflected back by the IPG 100 and detune these coils to some extent. These conditions would be interpreted by position indication circuitry 279 (FIG. 7B) to mean that an IPG 100 was present but misaligned with respect to the primary coil 130, specifically that the IPG 100 was closer to coils 230x1 and 230y1. External charger 210 could then indicate to the user to move the external charger 210 downwardly and to the left to improve charging alignment.

Figure 6A:
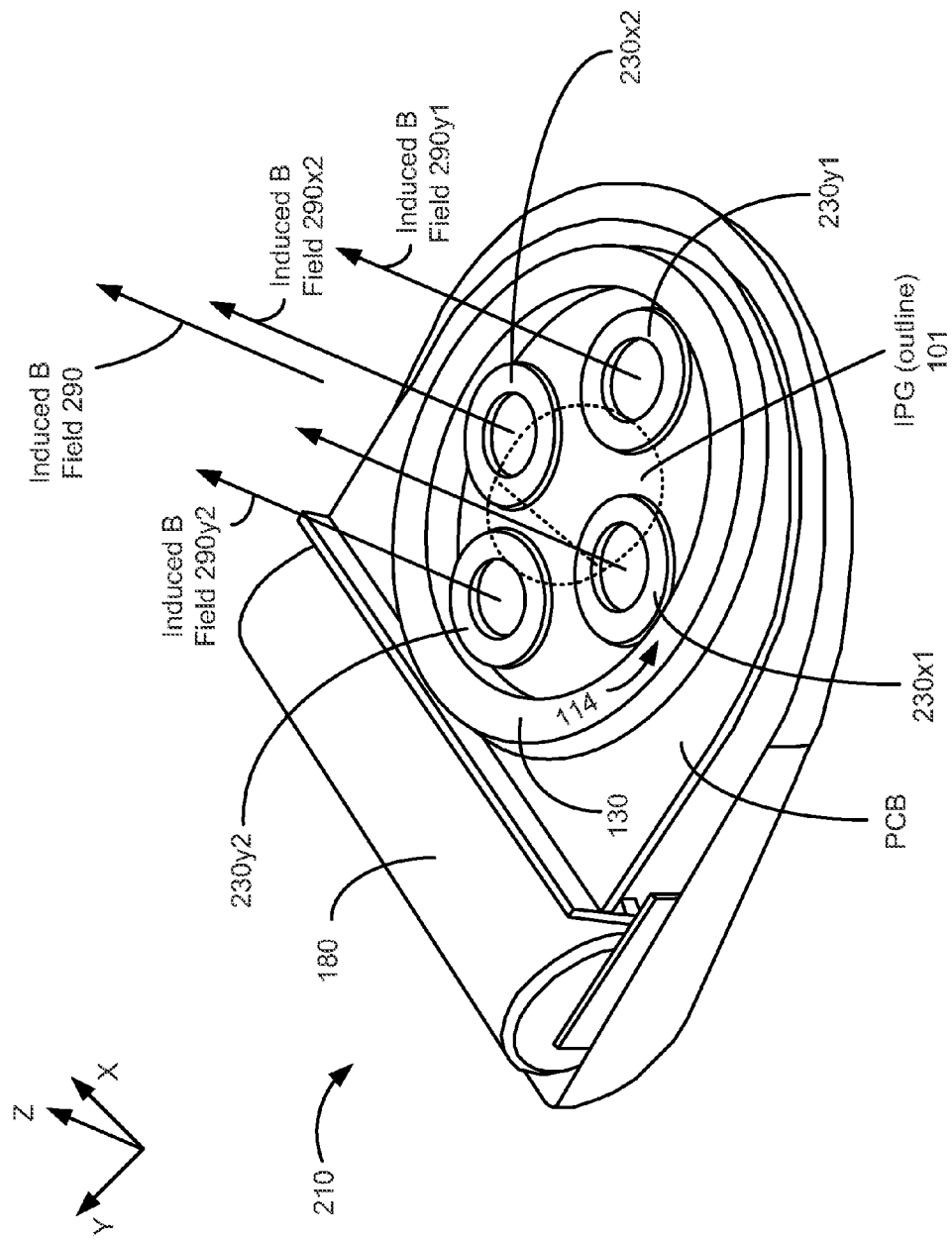
FIG. 6A shows a perspective view of one possible embodiment of an improved external charger for an implantable medical device wherein the position determination coils overlap with the outline of the implanted medical device.

In FIG. 6A, the PDCs are depicted as being large enough that they would overlap with the outline 101 of an IPG centered perfectly within them in the body. This would likewise produce the effect that each of the PDCs would be "detuned" in equal amounts by the presence of a perfectly aligned IPG 100. For example, when the charging coil 130 itself was "detuned" by the presence of the IPG 100, it would be able to indicate to the external charger 210's position indication circuitry 279 (FIG. 7B) that there was an implant somewhere under the surface of the skin in the vicinity of the external charger 210. At that point, the external charger 210 could activate the PDCs 230 to "fine tune" the alignment of the external charger 210 with the IPG 100. If each of the PDCs 230 were being driven at 10V, for example, the external charger 210 would indicate that it was properly centered over the IPG 100 when each of the PDCs 230 were simultaneously "detuned" by an equal amount, e.g., each of the PDCs 230 may register a voltage of 7V. If the external charger 210 were misaligned from IPG 100 in any direction, the PDCs 230 that were disproportionally closer to the IPG 100 would, due to the "detuning" effect, register disproportionally lower voltages than the PDCs 230 that were further away from the IPG 100. By comparing the voltages across each of the PDCs 230, position indication circuitry 279 (FIG. 7B) can indicate to the user the direction that the external charger 210 should be moved in to improve alignment.

Figure 6B:
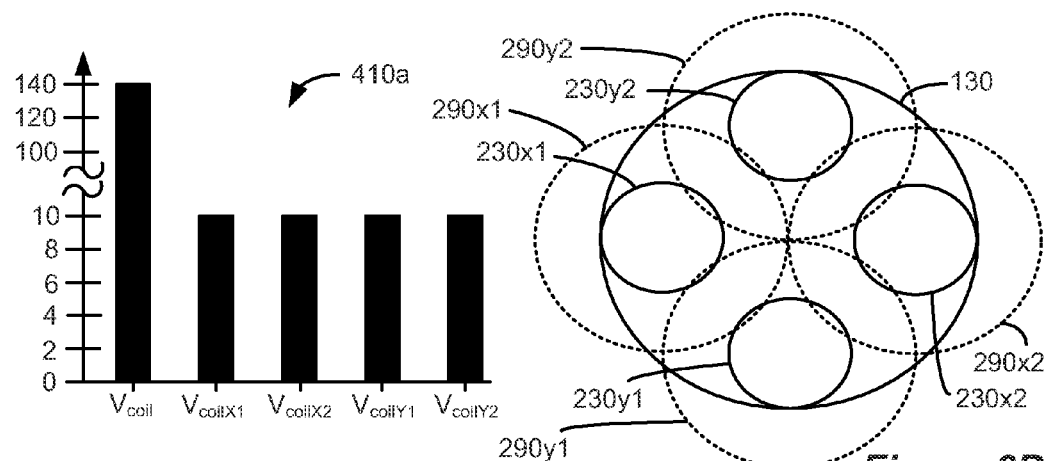
FIGS. 6B-6D show the effects on charging coil voltage and position determination coil voltage due to various charger/implant alignment scenarios.
Figure 6C:
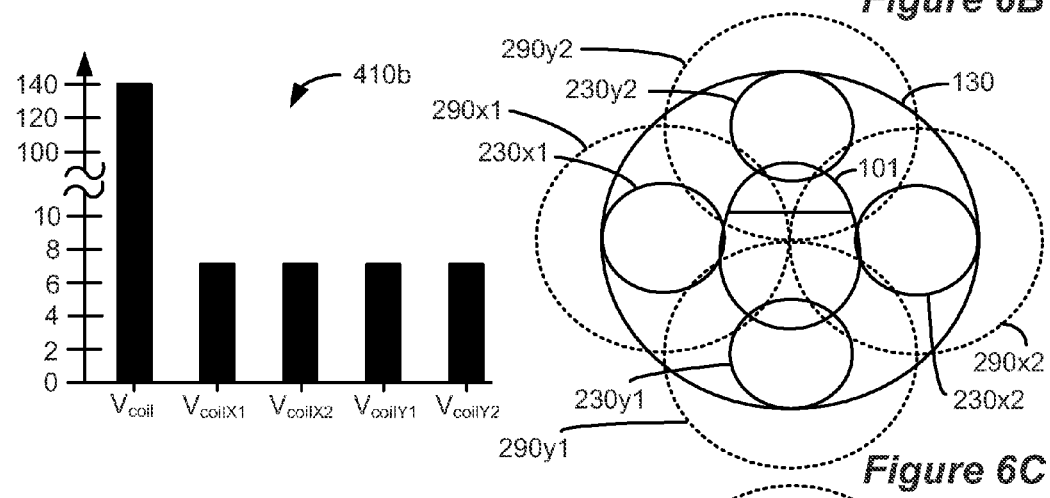
Figure 6D:
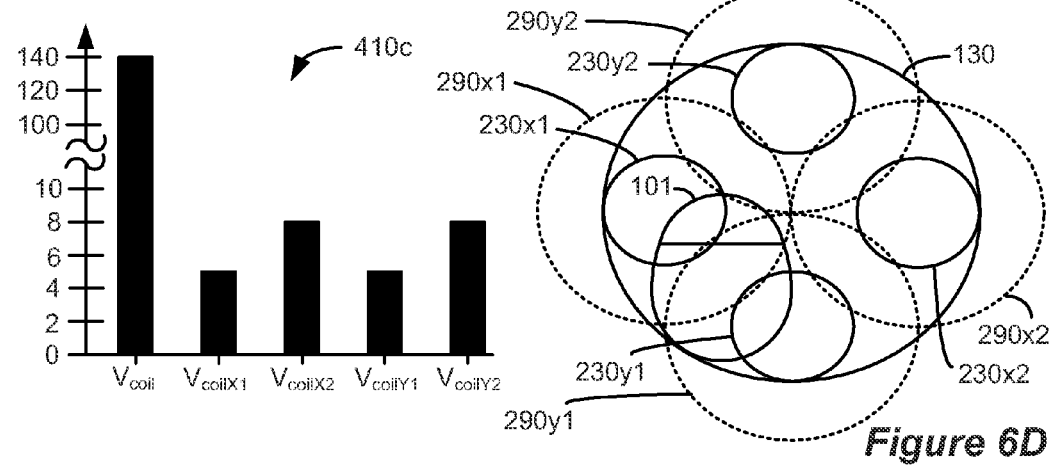

FIG. 6B-6D show in graphical form the "detuning" effects on the various coils of external charger 210 when an IPG 100 is placed in front of the external charger 210 of FIG. 6A. In FIG. 6B, there is no IPG 100 in the vicinity of the external charger 210's primary coil 130. Thus, there is no detuning of either the primary coil 130 or the PDCs 230. As such, Vcoil will register as whatever voltage the primary, i.e., charging, coil 130 is being driven at. In graph 410a, this is shown to be 140 volts. Likewise, the PDCs—VcoilX1, VcoilX2, VcoilY1, and VcoilY2—will register as approximately the voltage they are being driven at, with some deviation possible due to potential cross talk between the PDCs. In graph 410a, this is shown to be 10 volts. These conditions would be interpreted by position indication circuitry 279 (FIG. 7B) to mean that there was no IPG 100 present.

In FIG. 6C, by contrast, the IPG 100 is perfectly aligned within external charger 210's primary coil 130, shown by IPG outline 101. As such, Vcoil will register as being lower than the voltage that the primary, i.e., charging, coil 130 is being driven at due to the detuning effect of the IPG 100. In graph 410b, the charging coil is shown to be detuned from a value of 140 volts to a value of 100 volts, indicating the presence of an implanted IPG 100 in the vicinity of external charge 210. The PDCs—VcoilX1, VcoilX2, VcoilY1, and VcoilY2—in graph 410b are each registering a voltage less than they are being driven at. In graph 410b, this is shown to be 7 volts. This occurs because the IPG 100 is well-aligned with primary coil 130, and thus, each of the magnetic fields induced by the PDCs 230 are reflected back in equal amounts by the IPG 100, causing a substantially equal amount of detuning in each PDC 230. These conditions would be interpreted by position indication circuitry 279 (FIG. 7B) to mean that an IPG 100 was both present and well-aligned with respect to the primary coil 130. Due to the potentially asymmetrical nature of the IPG 100, the PDCs 230 may not each be detuned to exactly the same voltage when the IPG 100 is perfectly aligned. However, position indication circuitry 279 may store some threshold values at which it will determine that each of the PDCs is detuned by a sufficiently equal amount that the IPG 100 is well aligned with the primary coil 130.

In FIG. 6D, the IPG 100 is in the vicinity of external charger 210's primary coil 130, but is misaligned, as is shown by IPG outline 101. As such, Vcoil will register as being lower than the voltage that the primary, i.e., charging, coil 130 is being driven at due to the detuning effect of the IPG 100. In graph 410c, the charging coil is shown to be detuned from a value of 140 volts to a value of 100 volts, indicating the presence of an implanted IPG 100 in the vicinity of external charge 210. Two of the PDCs—VcoilX2 and VcoilY2—are still registering a voltage only minimally detuned from the voltage they are being driven at. In graph 410c, this is shown to be 8 volts. However, two of the PDCs—VcoilX1 and VcoilY1—have been detuned to a value of 5 volts. This occurs because the IPG 100 is closer to PDCs 230x1 and 230y1 than it is to the other PDCs. Thus, the magnetic fields induced by PDCs 230x1 and 230y1 are reflected back by the IPG 100 and detune these coils to some extent. These conditions would be interpreted by position indication circuitry 279 (FIG. 7B) to mean that there was an IPG 100 was present but misaligned with respect to the primary coil 130, specifically that the IPG 100 was closer to coils 230x1 and 230y1. External charger 210 could then indicate to the user to move the external charger 210 downwardly and to the left to improve charging alignment.

In FIGS. 6C and 6D, there may be some "cross talk" from one PDC 230 to another due to the PDC's relatively larger radii when compared to the embodiment shown in FIGS. 5A-5D, as is seen by the overlapping of the dashed magnetic field lines 290. One possible solution to this potential issue would be to adjust the expected voltages from each PDCs 230 when no IPG 100 is present. For example, through experimentation, it may be found that the cross talk with a perfectly centered IPG 100 may result in a baseline PDC voltage of 9V rather than 10V as is shown in FIG. 6B. Another solution to this issue may be to enable one PDC 230 at a time, rapidly cycling through each PDC, sensing the voltage across each PDC as it is enabled (See FIG. 8A).

Although it may be more difficult to determine when an external charger 210 is perfectly aligned using the embodiment of FIG. 6A than it is with the embodiment of FIG. 5A due to, e.g., the asymmetrical nature of the IPG 100, it may be necessary to increase the diameter of the PDCs, as is shown in FIG. 6A when compared to FIG. 5A, to achieve a satisfactory signal-to-noise ratio when alignment sensing circuitry 281 is attempting to measure the amount of "detuning" in the PDCs 230. Increasing the diameter of the PDCs 230 also allows the external charger 210 to detect a misaligned IPG 100 at a further distance from the charger, e.g., implanted in the body at a greater depth. However, increasing the diameter of the PDCs may also increase the amount of "cross talk" between each of the individual PDC coils 230.

Figure 7B:
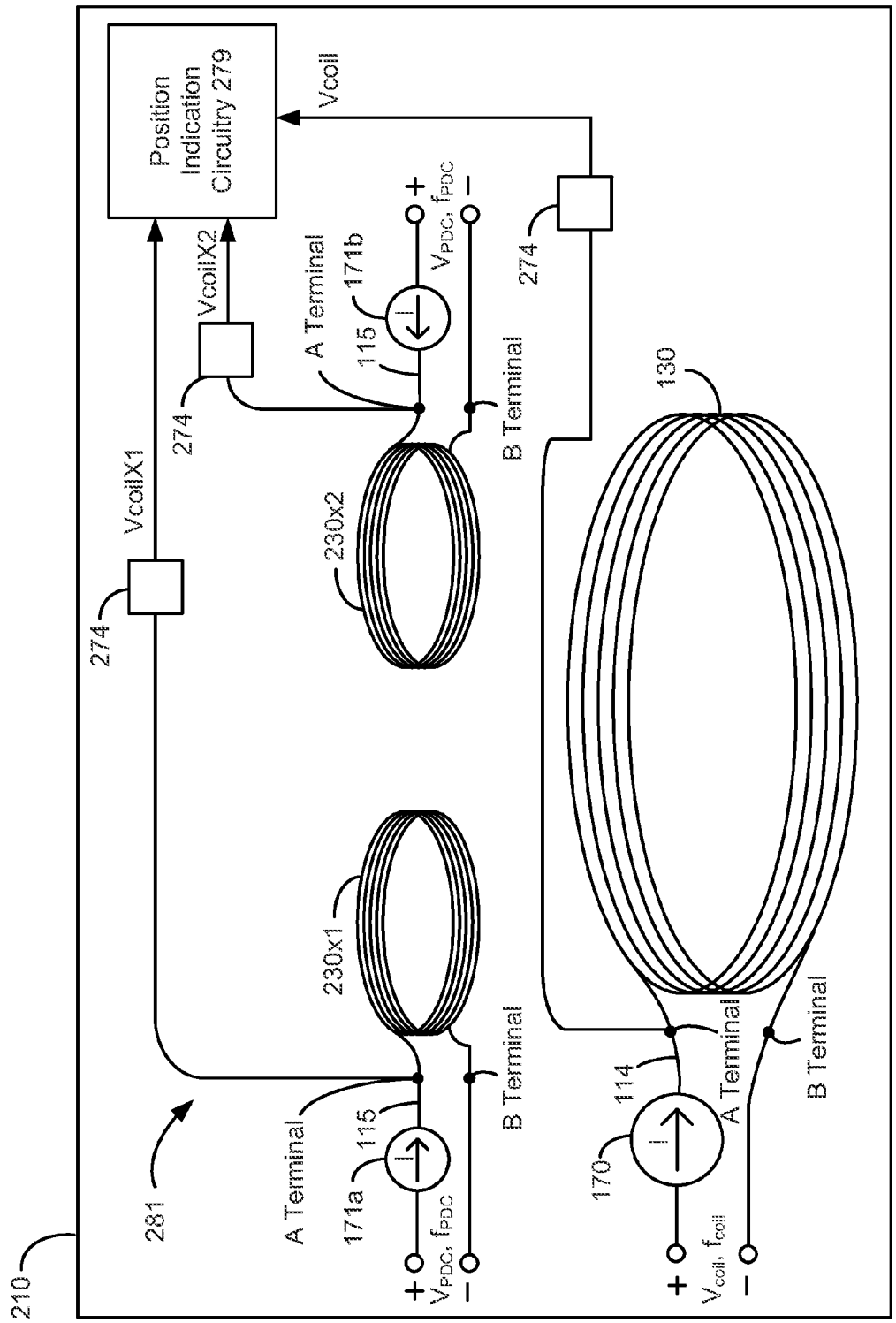
FIG. 7B shows two position determination coils whose outputs are sent to position indication circuitry.

FIG. 7A shows an improved external charger 210 with a primary coil 130 configured for transcutaneously charging the IPG 100 via inductive coupling and with PDCs 230 arranged in accordance with the embodiment shown in FIG. 6A. The improved external charger 210 comprises a primary coil 130, through which an AC current 114 is passed via an AC current source 170 at a frequency, $f_{coil}$. This current 114 produces induced magnetic field 290 (FIGS. 4A-4C). Improved external charger 210 further comprises a plurality of PDCs 230, through which an AC current 115 is passed via a plurality of AC current sources 171a-d at a frequency, $f_{PDC}$. In FIG. 7A, only a single AC current source is shown for simplicity. It is possible, and may be preferable, to drive each PDC 230 using a separate AC current source 171. However, the present disclosure also contemplates a system in which each of the PDCs 230 could be driven by a single AC current source 171 whose signal is fanned out to each of the PDCs 230. Current 115 from current sources 171a-d produces induced magnetic fields 290x1, 290x2, 290y1, 290y2 (FIGS. 5A, 6A), which are illustrated as a plurality of flux lines 160. By comparing electrical measurements, such as the amount of the "detuning" in the PDCs 230 due to the reflected magnetic field 295 passing through them, the position of the implant in both the x- and y-directions can be determined by the external charger 210's position indication circuitry 279 (FIG. 7B). Audio and/or visual feedback of the implant position can then be communicated to the patient to improve alignment of the charger.

FIG. 7B shows one potential arrangement of a pair of PDCs 230x for the improved external charger 210 that is depicted in FIGS. 5A and 6A. In this embodiment, only PDCs 230x1 and 230x2, which are used to determine the IPG 100's misalignment with the external charger 210 in the x-direction (and not PDCs 230y1 and 230y2), are shown for the sake of simplicity.

A complete external charger 210 utilizing this embodiment will also have a corresponding pair of PDCs 230y1 and 230y2 to measure misalignment in the y-direction. In the embodiment of FIG. 7B, each of the PDCs 230x1 and 230x2 are driven by their own current source 171. Further, each PDC in a PDC pair has one terminal connected to ground and the other terminal connected to a simple voltage divider circuit 274 that serves to divide down the voltage measured across the coil before sending the measured voltage value to position indication circuitry 279. As an alternative to measuring voltages, the position indication circuitry 279 could independently sense the strength of the current 115 passing through each PDC 230 to determine the amount of detuning in each PDC 230.

In the embodiment of FIG. 7B, the voltages (or currents) across each PDC within each PDC pair are compared to each other within the position indication circuitry 279 in order to determine the misalignment of the external charger 210 with respect to a particular direction. In other words, alignment sensing circuitry 281 derives a first indicator and a second indicator, wherein the first and second indicators indicate misalignment with respect to first and second directions. Position indication circuitry 279 can then determine the location of the implantable medical device 100 and deliver appropriate instruction to the user as to how to improve the external charger 210's alignment with the implantable medical device 100.

For example, if IPG 100 is closer in the x-direction to PDC 230x1 than it is to PDC 230x2, the voltage detected at PDC 230x1 will be lower, say 8V, than the voltage detected at PDC 230x2, say 10V. In this case, there would be a difference of positive two volts (VcoilX2−VcoilX1). If instead, the IPG 100 is closer in the x-direction to PDC 230x2, the voltage at PDC 230x1 will be higher, say 10V, than the voltage detected at PDC 230x2, say 8V. In this case, there would be a difference of negative two volts. The magnitude of the difference between VcoilX1 and VcoilX2 also indicates relative closeness of the primary coil 130 and the IPG 100. For example, if the voltages measured at 230x1 and 230x2 were 2V and 10V, respectively, instead of 8V and 10V as in the example above, the difference between the signals would be 8V. The greater magnitude of difference would indicate to position indication circuitry 279 that IPG 100 was located even further towards PDC 230x1 in the 2V/10V scenario than it was in the 8V/10V scenario. Thus, this embodiment is able to provide detailed information about the IPG 100's relative location in the x-direction. As will be understood, the same processing can simultaneously be carried out by PDCs 230y1 and 230y2 to determine the IPG 100's relative location in the y-direction, thus allowing external charger 210 to give a complete picture of IPG 100's location.

The embodiments of FIGS. 7A-7B show that the primary coil 130 is driven by an AC voltage of $V_{coil}$ at a frequency of $f_{coil}$, whereas the PDCs 230 are driven at a voltage of $V_{PC}$ at a frequency of $f_{PDC}$. In certain embodiments, it will be advantageous to drive the charging coil 130 and PDCs 230 at different frequencies. Because the field produced by the charging coil 130 is more powerful than the field produced by an individual PDC 230, if $f_{coil}$ were equal to $f_{PDC}$, it might be difficult for alignment sensing circuitry 281 to simultaneously determine the coil voltage at any of the PDCs 230 while the charge coil 130 is active because the charge coil 130's voltage might block out or "flood" the PDCs. Thus, in some embodiments, the charging coil 130 could be driven at, e.g., 140V and 80 kHz, whereas the PDCs 230 could be driven at, e.g., 10V and 800 kHz-1 MHz. The expected current draw of the charging coil 130 may be approximately 300 mA, whereas the expected current draw of each of the PDCs 230 might be 25 mA. Thus, the external charger 210 could possess at least two distinct signals sources—one signal for the charging coil 130, and one or more signals that can be routed to each of the PDCs 230. The charging coils are ideally driven at the smallest voltage possible so that the external charger 210's power source 180 expends a minimal amount of energy in powering them. It is also advantageous to ensure that the charging coil 130 and the PDCs 230 are driven at frequencies that are not direct integer harmonics of each other so that there is no interference when measuring the various coil voltages.

Figure 8A:
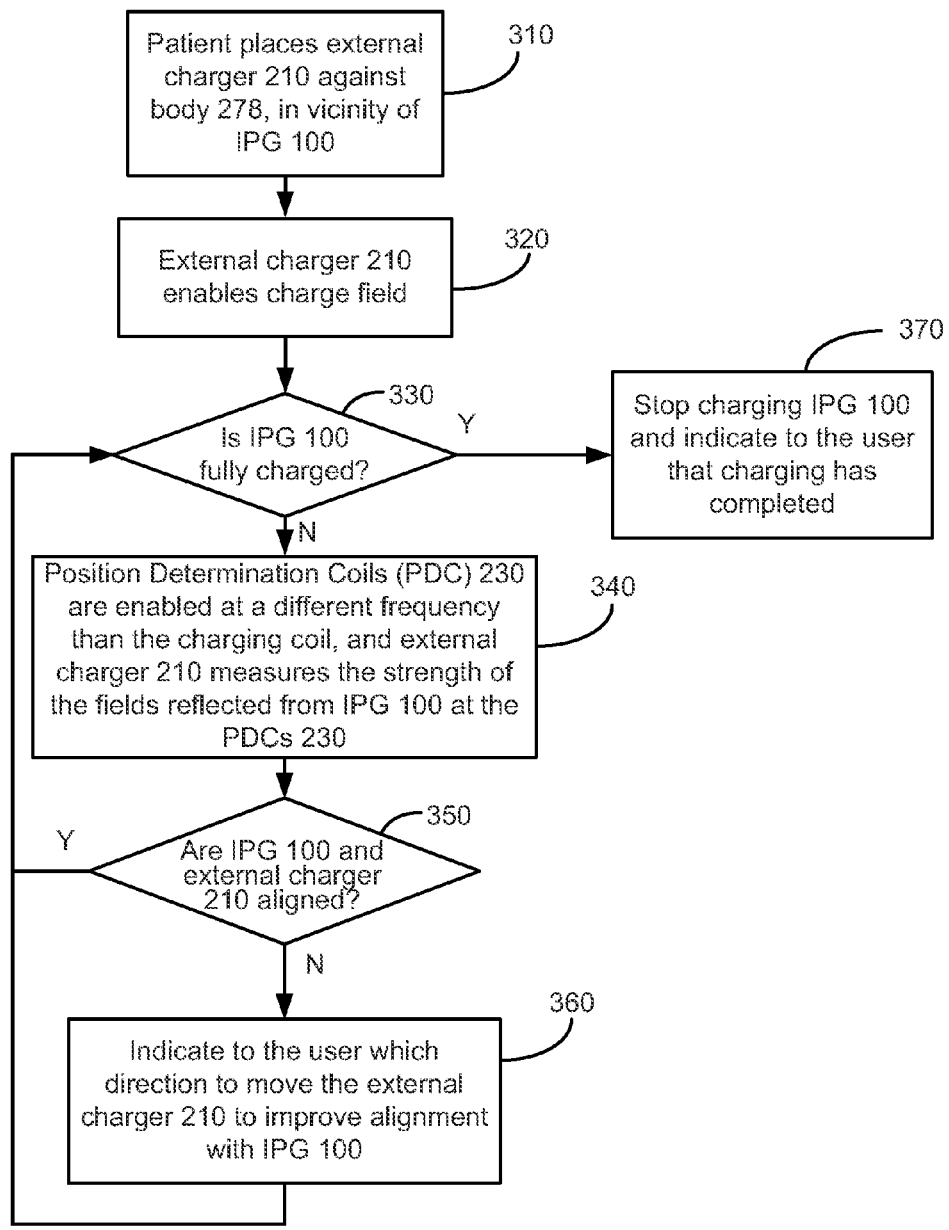
FIG. 8A is a flowchart detailing one embodiment of a technique for assuring the proper alignment of an external charger to an IPG wherein the charging coil and the position determination coils are driven at different frequencies.

FIG. 8A is a flowchart detailing one embodiment of a technique for assuring the proper alignment of an external charger 210 to an IPG 100, wherein the charging coil and the PDCs are driven by AC power sources at different, non-integer harmonic, frequencies—that is, $f_{coil}$ does not equal $f_{PDC}$. First, the user places external charger 210 against the surface of his body 278 in the known vicinity of IPG 100 (310). At this time, the patient will activate the external charger 210 and begin charging IPG 100 (320). The default setting for external charger 210 is maximum power output. As long as external charger doesn't receive an indication that IPG 100 is fully charged (330), it will continue to charge IPG 100. As external charger 210 is charging IPG 100 at a frequency of $f_{coil}$, alignment sensing circuitry 281 in the external charger 210 senses the charger's alignment with the IPG 100 based at least in part on electrical measurements taken from the plurality of PDCs 230 actively inducing magnetic fields at a frequency of $f_{PDC}$, and position indication circuitry 279 calculates the IPG 100's location (340). This calculation (340) occurs in real time so that, any time alignment becomes poor, corrective action can be indicated to the user and taken in subsequent steps. If IPG 100 and the external charger 210 are properly aligned (350), external charger 210 continues to charge the IPG 100's internal power source 180 until receiving indication that IPG 100 is fully charged (330). If the external charger 210 determines that IPG 100 and the external charger 210 are not properly aligned (350), the external charger 210 will indicate to the user which direction to move the external charger 210 to improve alignment (360) while still continuing to charge IPG 100. Once the external charger 210 determines that the IPG 100's internal power source 180 is fully charged (330), it will indicate via an audible beep or other visual indication to the user that the charging process has completed (370).

In other embodiments, it may be possible to drive the charging coil 130 and PDCs 230 at the same frequency. Because the field produced by the charging coil 130 is much more powerful than the field produced by an individual PDC 230, if $f_{coil}$ were to equal $f_{PDC}$, it might be difficult for alignment sensing circuitry 281 to simultaneously determine the coil voltage at any of the PDCs 230 while the charge coil 130 is active due to the charge coil 130's voltage blocking out or "flooding" the PDCs. Thus, in some embodiments, the charging coil 130 could be temporarily shut off to allow alignment sensing circuitry 281 to either sequentially or simultaneously measure the voltages at each of the PDCs 230 and send the measurements to the position indication circuitry 279. For example, the charging coil 130 could be deactivated and the PDCs 230 could be queried for 50-100 ms out of each second, with the charging coil activated for the remaining 900-950 milliseconds out of each second. In such an embodiment, the external charger 210 could possess a single AC signal source for driving the charging coil 130 and the PDCs 230 at a single frequency. The charging coils are ideally driven at the smallest voltage possible so that the external charger 210's power source 180 expends a minimal amount of energy in powering them.

Figure 8B:
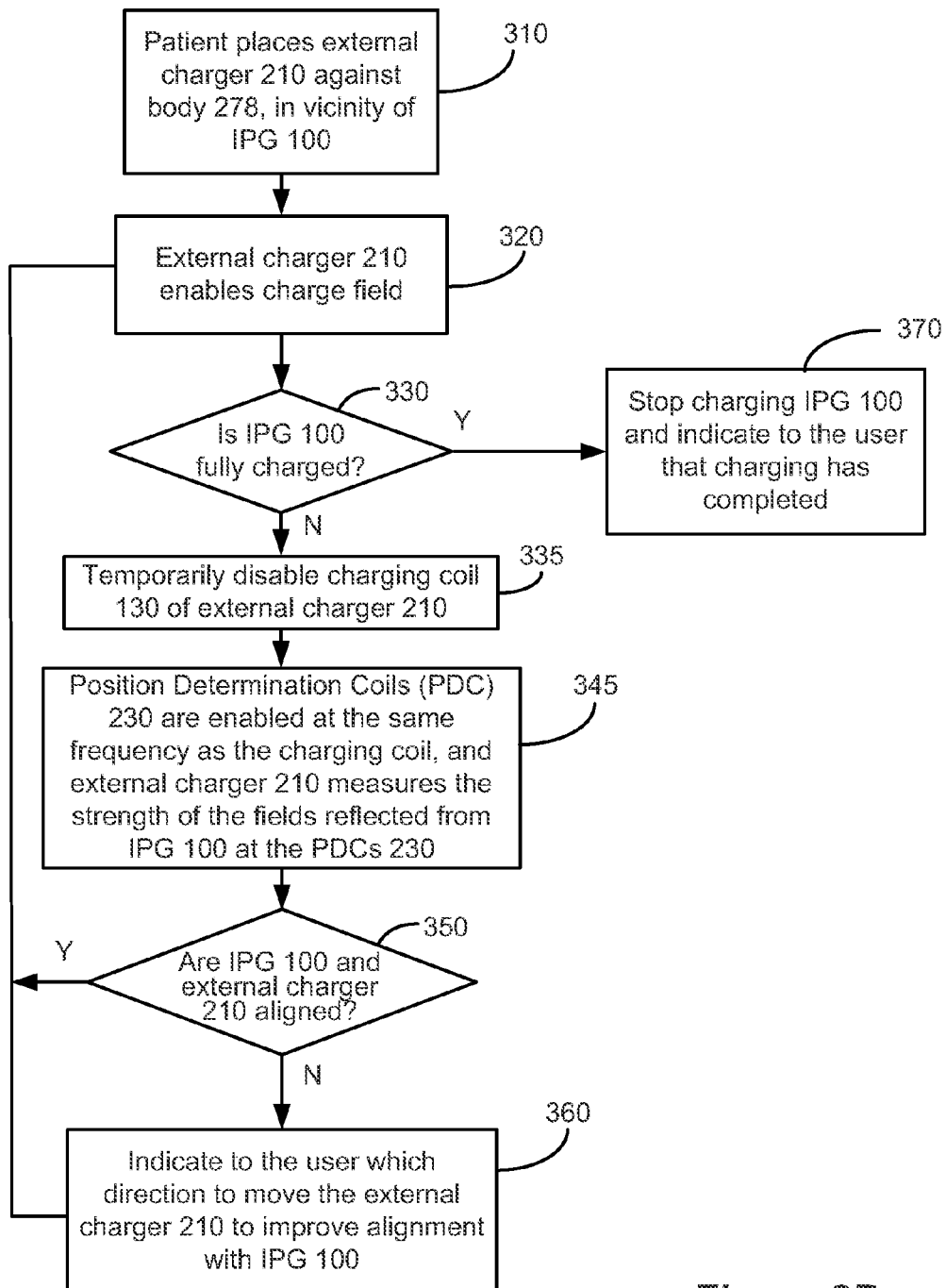
FIG. 8B is a flowchart detailing one embodiment of a technique for assuring the proper alignment of an external charger to an IPG wherein the charging coil and the position determination coils are driven at the same frequency.

FIG. 8B is a flowchart detailing one embodiment of a technique for assuring the proper alignment of an external charger 210 to an IPG 100, wherein the charging coil and the PDCs are driven by AC power sources at the same frequency—that is, $f_{coil}$ equals $f_{PDC}$. First, the user places external charger 210 against the surface of his body 278 in the known vicinity of IPG 100 (310). At this time, the patient will activate the external charger 210 and begin charging IPG 100 (320). The default setting for external charger 210 is maximum power output. As long as external charger doesn't receive an indication that IPG 100 is fully charged (330), it will continue to charge IPG 100. For a predetermined time interval, external charger 210 will temporarily disable charging coil 130 so that it can take measurements from the PDCs 230 (335). While external charger 210 has temporarily ceased charging IPG 100 at a frequency of $f_{coil}$, alignment sensing circuitry 281 in the external charger 210 senses the charger's alignment with the IPG 100 based at least in part on electrical measurements taken from the plurality of PDCs 230 actively inducing magnetic fields at a frequency of $f_{coil}$, and position indication circuitry 279 calculates the IPG 100's location (345). This calculation (345) occurs in real time so that, any time alignment becomes poor, corrective action can be indicated to the user and taken in subsequent steps. If IPG 100 and the external charger 210 are properly aligned (350), external charger 210 resumes charging the IPG 100's internal power source 180 until receiving indication that IPG 100 is fully charged (330). If the external charger 210 determines that IPG 100 and the external charger 210 are not properly aligned (350), the external charger 210 will indicate to the user which direction to move the external charger 210 to improve alignment (360) while still resuming its charging of IPG 100. Once the external charger 210 determines that the IPG 100's internal power source 180 is fully charged (330), it will indicate via an audible beep or other visual indication to the user that the charging process has completed (370).

Figure 9A:
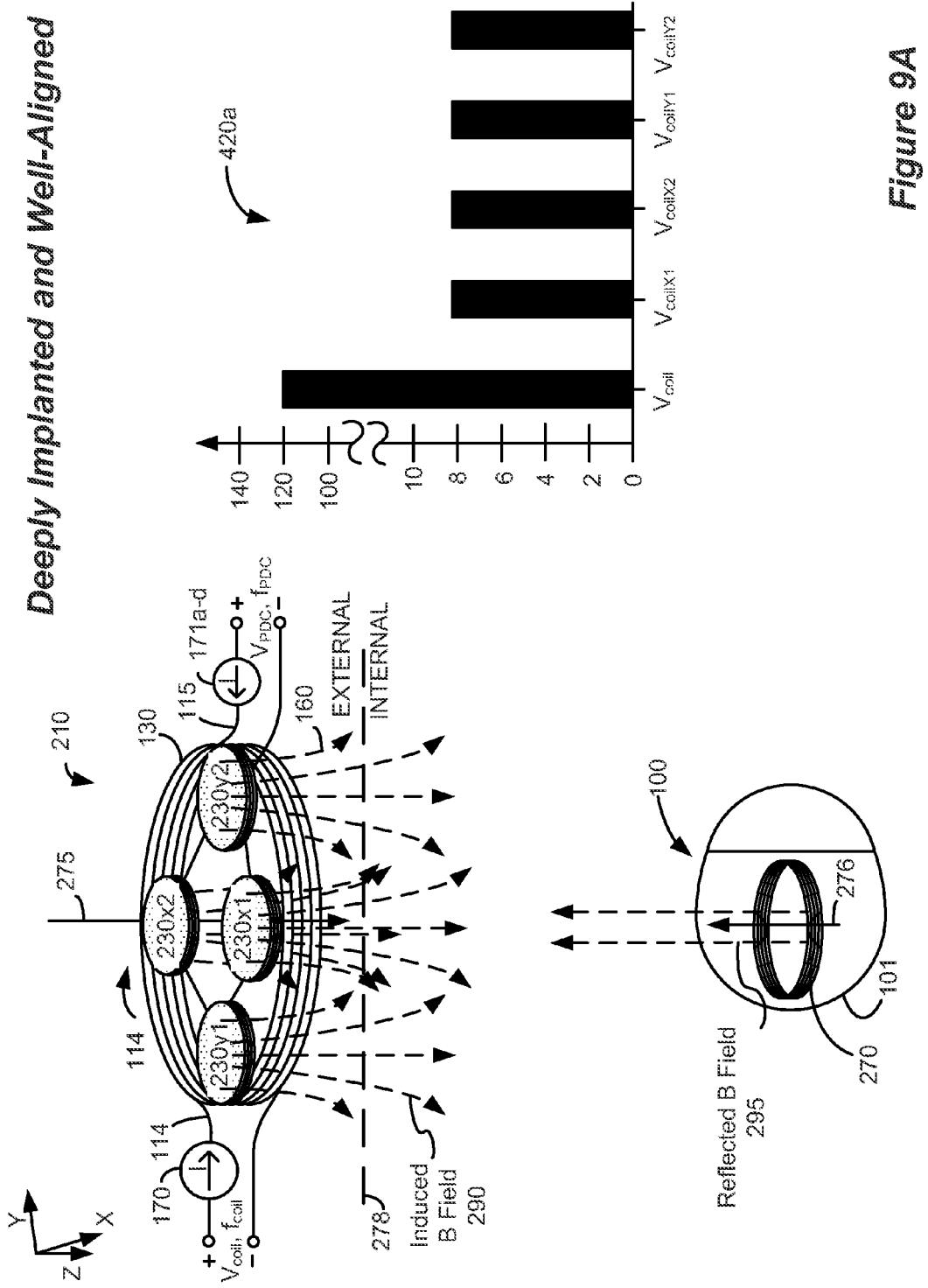

FIG. 9A shows a scenario where an implantable medical device 100 is deeply implanted in the patient's body but well aligned with external charger 210. In this scenario, the primary coil would be slightly detuned by the presence of the IPG (e.g., detuned from 140V to 120V), and each of the PDCs 230 would have a similar Vcoil because each coil would pick up an equivalent reflected magnetic flux, i.e., VcoilX1, VcoilX2, VcoilY1, and VcoilY2 would all be equal, as is shown in graph 420a of FIG. 9A (e.g., each is detuned from 10V to 8V). Thus, the differences between the measured voltages of the two PDCs in each of the PDC pairs would be zero or close to zero, and the position indication circuitry 279 would determine that the external charger 210 was properly, i.e., symmetrically, aligned with the IPG 100.

FIG. 9B shows a scenario where an implantable medical device 100 is shallowly implanted in the patient's body but poorly aligned with external charger 210; specifically, it is skewed in the y-direction. As discussed above, a prior art external charger would not be able to distinguish between the scenario presented in FIG. 9A and the scenario presented in FIG. 9B because the only measurement available would be Vcoil, which is 120V in both scenarios. However, with the improved external charger 210, these two scenarios are distinguishable. In the scenario shown in FIG. 9B, field PDC 230y2 measures a lower Vcoil (VcoilY2) than the other PDCs because PDC 230y2 picks up a disproportionately larger amount of reflected magnetic flux, as is shown in graph 420b of FIG. 9B (e.g., VcoilY2 is detuned from 10V to 6V, VcoilY1 is not detuned at all, and VcoilX1 and VcoilX2 are only minimally detuned). As was discussed above, the alignment sensing circuitry 281 can compare the VcoilY1 and VcoilY2 values. In this scenario, it would result in a determination that VcoilY2 is smaller than VcoilY1 and alignment sensing circuitry 281 would send signals to position indication circuitry 279 that would be interpreted to mean that the IPG 100 was actually closer to PDC 230y2 than it was to PDC 230y1, i.e., that the charger 210 was too far to the left as illustrated. The external charger 210 would then indicate to the user how to correct the alignment problem, i.e., by instructing the user to move the charger 210 to the right, to maximize the electrical coupling of external charger 210 and implantable medical device 100. The same processing is simultaneously carried out by PDCs 230x1 and 230x2 to report information about the IPG 100's location in the x-direction.

Figure 1:
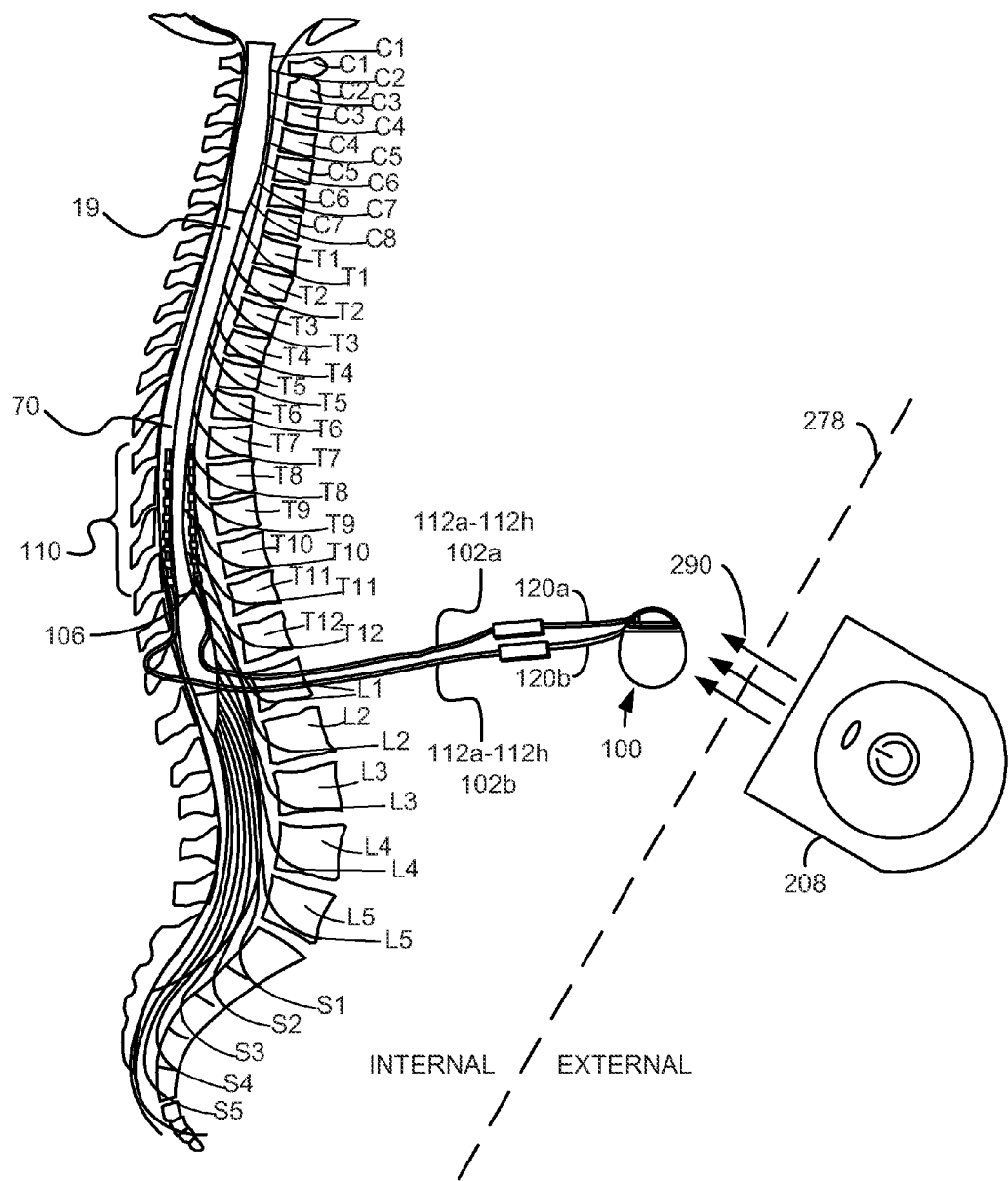
FIG. 1 shows an implantable pulse generator (IPG), an external charger, and the manner in which an electrode array is coupled to the IPG, in accordance with the prior art.
Figure 2:
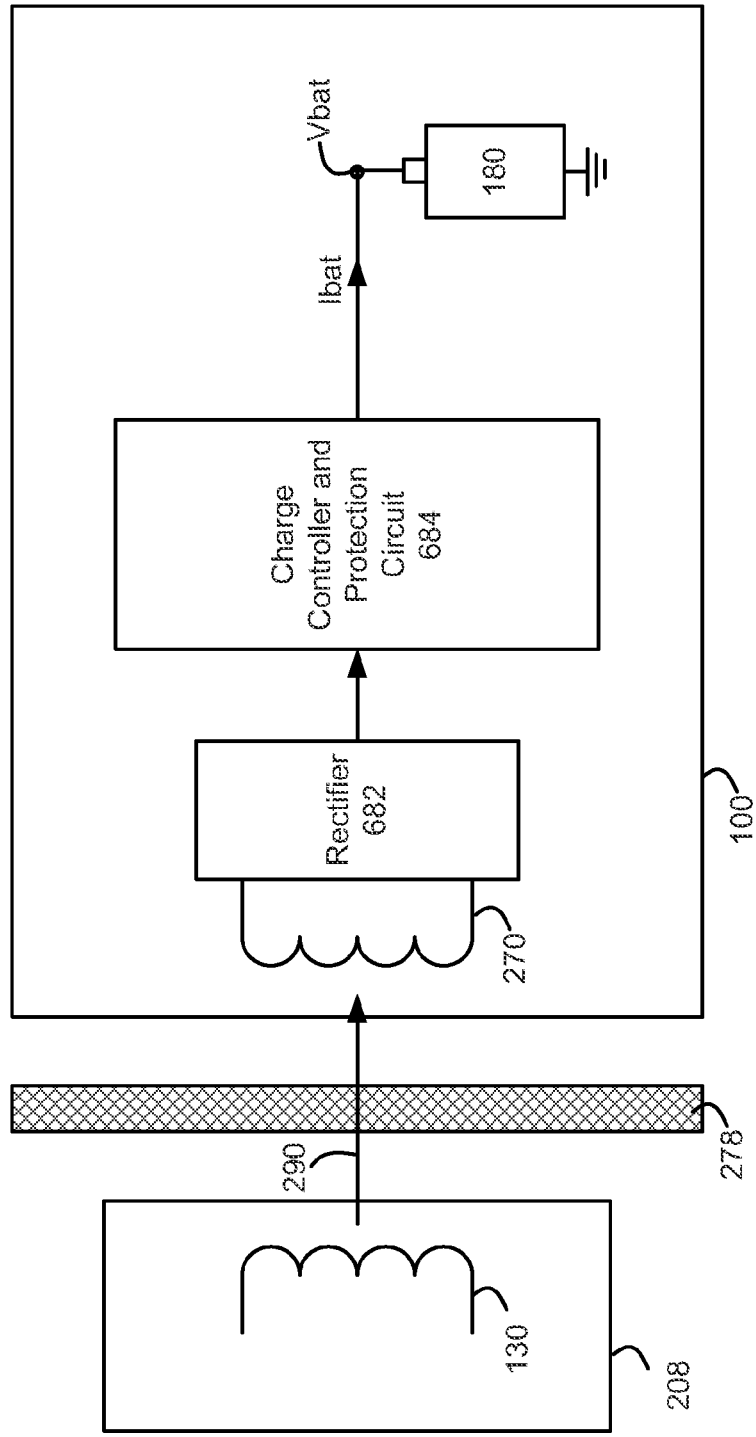
FIG. 2 illustrates a prior art system comprising an external charger for charging an implantable pulse generator, including the charge controller and battery protection aspects of the IPG.
Figure 3:
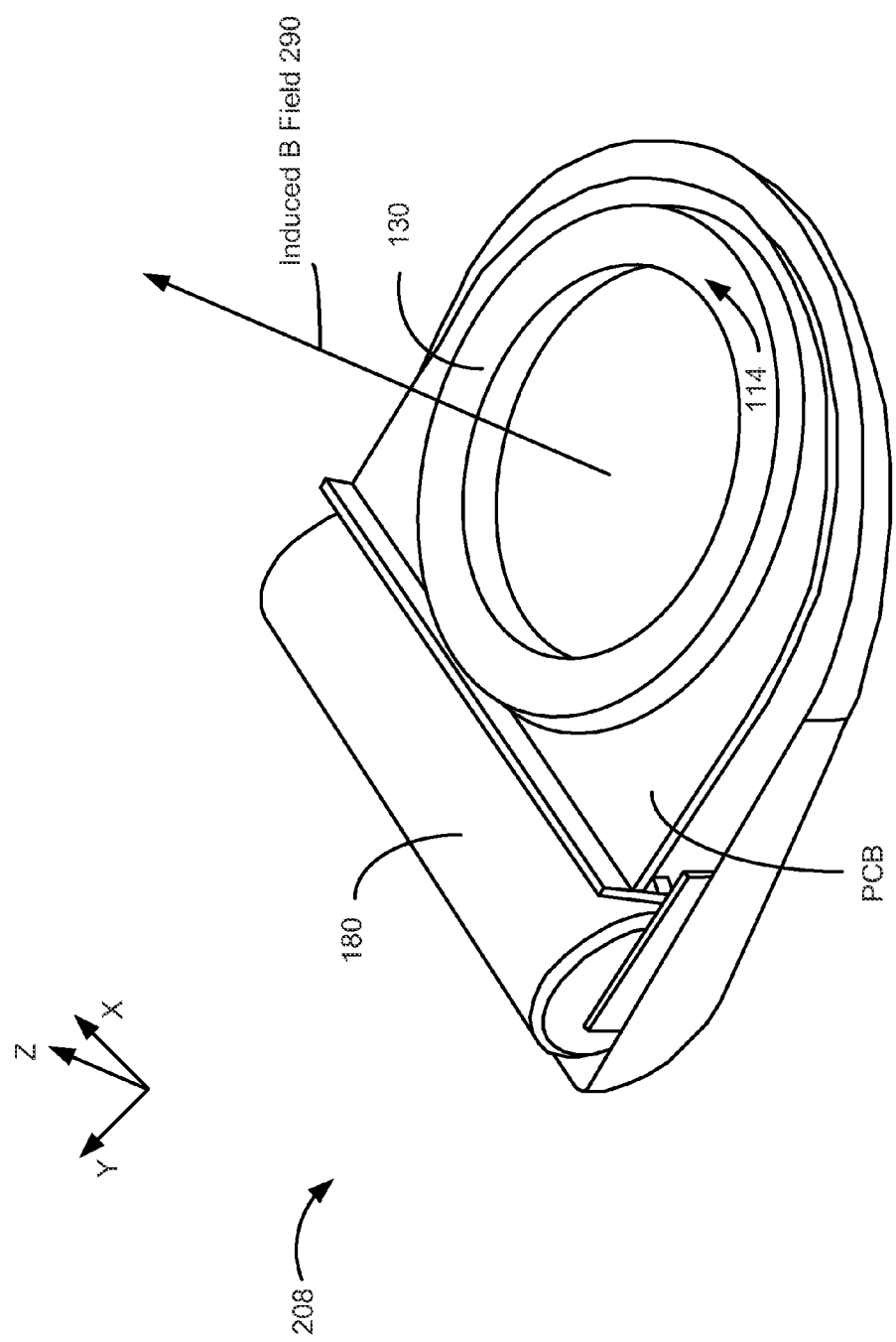
FIG. 3 shows a perspective view of a prior art external charger for an implantable medical device.

FIG. 10 shows a block diagram of an improved alignment detection system comprising an improved external charger 210 for inducing a magnetic field, including magnetic field-inducing PDCs 230, alignment sensing circuitry 281 for measuring reflections of the induced magnetic fields, and the position indication circuitry 279. The implantable device's circuitry 228 is similar to that described in reference to FIG. 2 above, and is shown in a block for simplicity. Alignment sensing circuitry 281 comprises the circuitry for reading the PDCs 230 and may be affixed to the printed circuit board (PCB) of the external charger 210. Alignment sensing circuitry 281 sends the PDC information to the position indication circuitry 279, which discerns the alignment between the implanted device 100 and the external charger 210. Position indication circuitry 279 then indicates to the user a direction in which the external charger 210 should be moved to improve the alignment of the external charger 210 relative to the implantable medical device 100. Such indication may occur in a variety of ways, including, but not limited to: activating visual indicators, such as LED lights 293 which can be configured to light up on the surface of the external charger 210 (See FIG. 11); activating audible indicators, such as beeps or verbal commands to the user; or activating tactile indicators, such as vibrating certain sides of the external charger 210 to indicate that the external charger 210 needs to be moved in that direction.

Because external charger 210 is often placed against a patient's back or buttocks, it can be difficult for the patient to receive information from the external charger 210 indicating how to improve the charger's alignment. To provide better positioning information to the patient, the external charger 210 may optionally transmit, via communications link 250, misalignment information to another external device for controlling the therapeutic settings of the implantable medical device, e.g., remote control 218. The external device may then indicate how the external charger 210 should be moved to improve the alignment of the external charger 210 relative to the implantable medical device 100. This type of communication is disclosed in commonly-owned U.S. patent application Ser. No. 12/476,523, filed Jun. 2, 2009.

Figure 11:
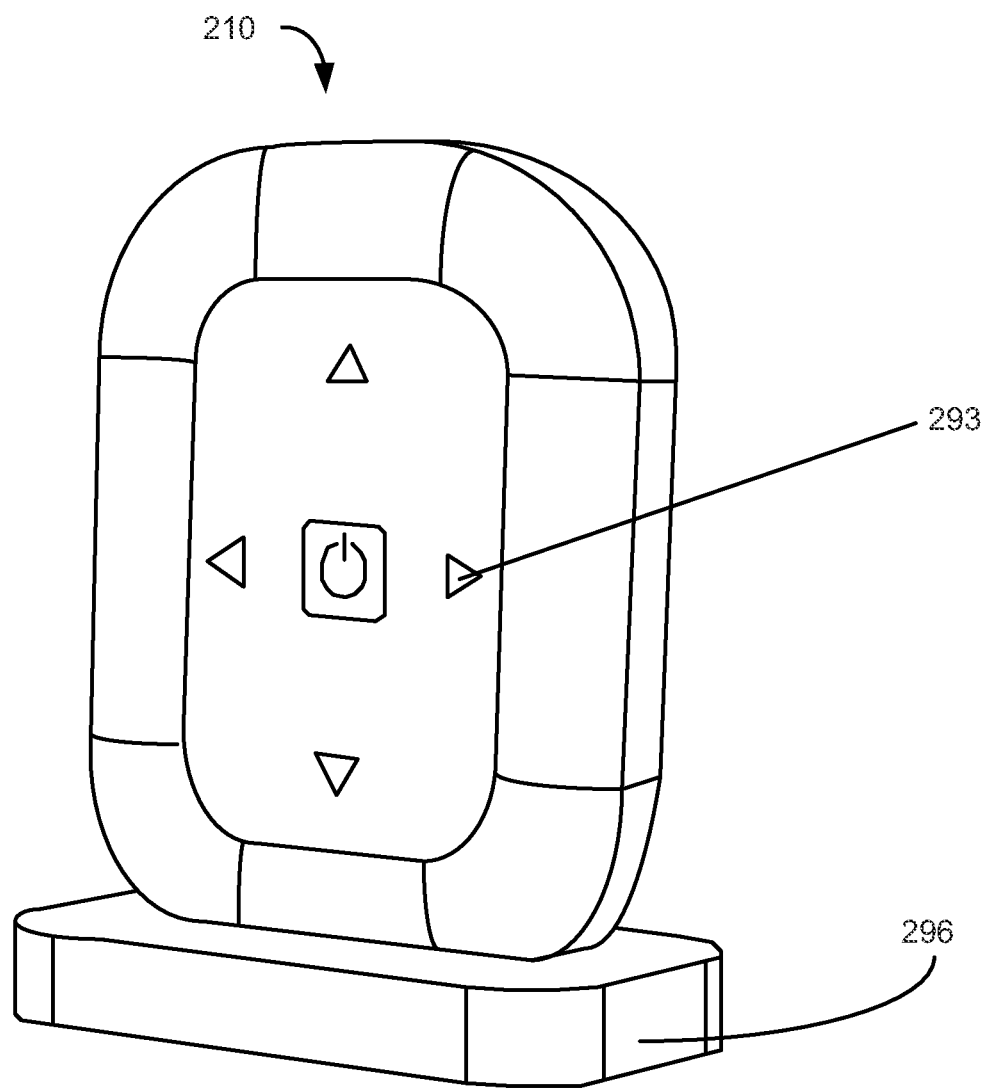
FIG. 11 shows one embodiment of an improved external charger for charging an implantable pulse generator.

FIG. 11 shows one embodiment of an improved external charger 210 for charging an implantable device. The external charger 210 is shown sitting in a base unit 296. In this embodiment, four arrow-shaped LED lights 293 are arranged on the surface of the external charger 210, with one arrow-shaped LED light pointing towards each edge of external charger 210. As position indication circuitry 279 determines in which direction the external charger 210 should be moved to provide better alignment with implantable device 100, it can send an appropriate control signal to illuminate one or more of the LED lights 293 to indicate that direction to the user. When position determination circuitry 279 has detected that there is a satisfactory degree of alignment between the external charger 210's primary coil 130 and the implantable device, position indication circuitry 279 will send a control signal to turn off each LED light 293 until it again senses a misalignment condition during charging.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger for providing power to an implantable medical device, comprising:
   one or more current or voltage sources configured to provide a plurality of currents that produce a plurality of magnetic fields at different locations in the external charger;
   an alignment sensing circuit configured to determine an alignment of the external charger relative to the implantable medical device, wherein the determination is based on electrical measurements for each of the plurality of currents taken from the one or more current or voltage sources; and
   at least one indicator, wherein the at least one indicator indicates the determined alignment of the external charger relative to the implantable medical device.

2. The external charger of claim 1, wherein the at least one indicator is visual.

3. The external charger of claim 2, wherein the at least one visual indicator indicates a direction in which the external charger should be moved to improve the alignment of the external charger relative to the implantable medical device.

4. The external charger of claim 1, wherein the electrical measurements are indicative of reflections of the magnetic fields from the implantable medical device.

5. The external charger of claim 1, wherein the one or more current or voltage sources comprise one or more current sources, and wherein the electrical measurements comprises voltages used by the one or more current sources to provide each of the plurality of currents.

6. The external charger of claim 1, wherein the one or more current or voltage sources comprise one or more voltage sources, and wherein the electrical measurements comprises the magnitude of the plurality of currents provided by the one or more voltage sources.

7. The external charger of claim 1, further comprising a primary coil, wherein the primary coil is configured to produce a primary coil magnetic field to provide power to the implantable medical device, wherein a central axis of the primary coil magnetic field and central axes of the plurality of magnetic fields are parallel.

8. The external charger of claim 7, wherein the primary coil magnetic field has a first frequency, the plurality of magnetic fields have second frequencies, and the first frequency is different from the second frequency.

9. The external charger of claim 7, wherein the central axes of the plurality of magnetic fields are equidistant from the central axis of the primary coil magnetic field at the different locations.

10. The external charger of claim 1, wherein the plurality of currents are provided to a plurality of coils at the locations.

11. The external charger of claim 1, comprising a plurality of current or voltage sources, each configured to provide one of the plurality of currents.

12. The external charger of claim 1, comprising a single current or voltage source for providing each of the plurality of currents.

13. A method for providing power to an implantable medical device using an external charger, comprising:
- providing a first magnetic field from the external charger to provide power to the implantable medical device;
- providing from one or more current or voltage sources a plurality of currents that produce a plurality of second magnetic fields at different locations in the external charger; and
- determining an alignment of the external charger relative to the implantable medical device, wherein the determination is based on electrical measurements taken from the one or more current or voltage sources; and
- indicating the determined alignment to a user.

14. The method of claim 13, wherein determining the alignment comprises determining a direction to move the external charger to improve the alignment of the external charger relative to the implantable medical device.

15. The method of claim 14, further comprising transmitting to another external device the determined direction.

16. The method of claim 15, wherein the another external device comprises an external device for controlling the therapeutic settings of the implantable medical device.

17. The method of claim 14, wherein indicating the determined alignment to a user comprises indicating the determined direction to a user.

18. The method of claim 13, wherein the locations occur in pairs, wherein the electrical measurements taken from the one or more current or voltage sources providing the currents to a first pair of locations indicate the alignment with respect to a first direction, and wherein the electrical measurements taken from the one or more current or voltage sources providing the currents to a second pair of locations indicate the alignment with respect to a second direction orthogonal to the first direction.

19. The method of claim 18, wherein the one or more current or voltage sources comprise one or more current sources, and wherein determining the alignment comprises:
- comparing voltages used to provide the currents in the first pair to produce a first error indication with respect to the first direction, and
- comparing voltages used to provide the currents in the second pair to produce a second error indication with respect to the second direction.

20. The method of claim 18, wherein the one or more current or voltage sources comprise one or more voltages sources, and wherein determining the alignment comprises:
- comparing magnitudes of the currents in the first pair to produce a first error indication with respect to the first direction, and
- comparing magnitudes of the currents in the second pair to produce a second error indication with respect to the second direction.

21. The method of claim 13, wherein the first magnetic field is provided by a primary coil in the external charger.

22. The method of claim 13, wherein the second magnetic fields are provided by coils at the different locations.

23. The method of claim 13, wherein the first magnetic field and the plurality of second magnetic fields have different frequencies.

24. The method of claim 13, wherein second central axes of the plurality of second magnetic fields are equidistant from a first central axis of the first magnetic field at the different locations.

25. The method of claim 13, wherein second central axes of the plurality of second magnetic fields and a first central axis of the first magnetic field are parallel.

26. The method of claim 13, wherein at least two of the plurality of currents are provided by different current or voltage sources.

27. The method of claim 13, wherein at least two of the plurality of currents are provided by the same current or voltage source.

28. The method of claim 13, wherein the electrical measurements comprises voltages used to produce the currents.

29. The method of claim 13, wherein the electrical measurements comprise magnitudes of the plurality of currents.

30. The method of claim 13, wherein the electrical measurements are taken simultaneously.

31. The method of claim 13, wherein the power provided to the implantable medical device is temporarily interrupted to take the electrical measurements.

32. An external charger for providing power to an implantable medical device, comprising:
- one or more current or voltage sources configured to provide a plurality of currents that produce a plurality of magnetic fields at different locations in the external charger; and
- an alignment sensing circuit configured to determine an alignment of the external charger relative to the implantable medical device, wherein the determination is based on electrical measurements for each of the plurality of currents taken from the one or more current or voltage sources;
- a primary coil, wherein the primary coil is configured to produce a primary coil magnetic field to provide power to the implantable medical device, wherein a central axis of the primary coil magnetic field and central axes of the plurality of magnetic fields are parallel,
- wherein the primary coil magnetic field has a first frequency, the plurality of magnetic fields have second frequencies, and the first frequency is different from the second frequency.

* * * * *